US007619106B2

(12) United States Patent
Damrau et al.

(10) Patent No.: US 7,619,106 B2
(45) Date of Patent: Nov. 17, 2009

(54) PREPARATION OF PARTIALLY HYDROGENATED RAC-ANSA-METALLOCENE COMPLEXES

(75) Inventors: Hans-Robert-Hellmuth Damrau, Constance (DE); Patrik Müller, Ludwigshafen (DE); Valerie Garcia, Compiègne (FR); Christian Sidot, Compiègne (FR); Christian Tellier, Campiègne (FR); Stéphanie Duchiron, Lyons (FR); Jean-Francois Lelong, Tracy-le-Mont (FR)

(73) Assignee: Basell Polyolefine GmbH, Wesseling (DE)

( * ) Notice: Subject to any disclaimer, the term of this patent is extended or adjusted under 35 U.S.C. 154(b) by 357 days.

(21) Appl. No.: 10/532,523

(22) PCT Filed: Oct. 22, 2003

(86) PCT No.: PCT/EP03/11679

§ 371 (c)(1),
(2), (4) Date: May 28, 2007

(87) PCT Pub. No.: WO2004/037838

PCT Pub. Date: May 6, 2004

(65) Prior Publication Data

US 2008/0200708 A1 Aug. 21, 2008

Related U.S. Application Data

(60) Provisional application No. 60/431,806, filed on Dec. 9, 2002.

(30) Foreign Application Priority Data

Oct. 25, 2002 (DE) ................ 102 50 025

(51) Int. Cl.
C07F 17/00 (2006.01)
B01J 31/00 (2006.01)
C08F 4/44 (2006.01)

(52) U.S. Cl. ............... 556/11; 534/15; 556/12; 556/28; 556/43; 556/53; 556/58; 502/103; 526/943

(58) Field of Classification Search .......... 534/15; 556/11, 12, 28, 43, 53, 58
See application file for complete search history.

(56) References Cited

U.S. PATENT DOCUMENTS

| 4,769,510 | A | | 9/1988 | Kaminsky et al. | |
| 5,304,614 | A | | 4/1994 | Winter et al. | |
| 5,442,119 | A | | 8/1995 | Buchwald et al. | |
| 5,883,275 | A | | 3/1999 | Bingel et al. | |
| RE37,208 | E | * | 6/2001 | Winter et al. | 526/348 |
| 6,262,286 | B1 | * | 7/2001 | Gregorius et al. | 556/11 |
| 6,992,204 | B2 | * | 1/2006 | Damrau et al. | 556/53 |
| RE39,532 | E | * | 3/2007 | Winter et al. | 556/53 |
| 7,193,099 | B2 | * | 3/2007 | Damrau et al. | 556/11 |
| RE39,561 | E | * | 4/2007 | Winter et al. | 556/53 |
| 2004/0010157 | A1 | * | 1/2004 | Damrau et al. | 556/43 |
| 2005/0182266 | A1 | * | 8/2005 | Schulte et al. | 556/11 |
| 2006/0154804 | A1 | * | 7/2006 | Schottek et al. | 502/103 |

FOREIGN PATENT DOCUMENTS

| DE | 100 30 638 | 1/2002 |
| EP | 0 185 918 | 7/1986 |
| EP | 0 344 887 | 12/1989 |
| EP | 0 537 686 | 4/1993 |
| EP | 0 581 754 | 2/1994 |
| EP | 0 643 079 | 3/1995 |
| EP | 0 700 935 | 3/1996 |
| EP | 0 839 822 | 5/1998 |
| JP | 07-41521 | 2/1995 |
| JP | 07-292019 | 11/1995 |
| WO | WO-92/09545 | 6/1992 |
| WO | WO-99/15538 | 4/1999 |
| WO | WO-02/00672 | 1/2002 |

OTHER PUBLICATIONS

Rheingold, A. L. et al, "Preparation and Properties of Chiral Titanocene and Zirconocene Dichloride Complexes of a Chiral Ligand", Organometallics (1992), vol. 11, pp. 1869-1876.

Schupfner, G. et al., "Microstructure Of Polypropene Samples Produced With Different Homogeneous Bridged Indenyl Zirconium Catalysts. Clues on The Structure And Reactivity Relation", Journal of Molecular Catalysis A: Chemical 102 (1995), pp. 59-65.

Habaue, S. et al., "Polymerization And Asymmetric Oligomerization Of Allylsilanes Using Chiral Ethylenebis(4,5,6,7-tetrahydro-1-indenyl)zirconium and -hafnium Complexes", Macromol. Chem. Phys. (1998), vol. 199, pp. 2211-2215.

Polo, E. et al., "Ethene/propene Copolymerisations With rac-EBTHIZrR$_2$/alumoxane: α-ligands Effect", Journal of Molecular Catalysis A: Chemical 160 (2000), pp. 229-236.

Schmidt, K. et al., "Photochemical Isomerization of Me$_2$Si-Bridged Zirconocene Complexes. Application to Stereoselective Syntheses of ansa-Zirconocene binaphtholate Stereoisomers", Organometallics (1997), vol. 16, pp. 1724-1728.

(Continued)

*Primary Examiner*—Porfirio Nazario Gonzalez
(74) *Attorney, Agent, or Firm*—William R Reid

(57) ABSTRACT

The invention relates to a process for preparing hydrogenated or partially hydrogenated, racemic ansa-metallocene complexes by reacting bridged or unbridged transition metal complexes with alkali metal compounds or alkaline earth metal compounds, heating the resulting reaction mixture to a temperature in the range from −78 to 250° C. and at least partially hydrogenating the reaction products in the presence of a suitable catalyst, to the corresponding hydrogenated or partially hydrogenated metallocenes and to their use as catalysts or as a constituent of catalysts for the polymerization of olefinically unsaturated compounds or as reagents or catalysts in stereoselective synthesis.

7 Claims, No Drawings

OTHER PUBLICATIONS

Busico, V. et al., "Propene Polymerication Promoted by $C_2$-symmetric Metallocene Catalysts: From Atactic to Isotactic Polypropene in Consequence of an Isotope Effect", J. Am. Chem. Soc. (1996), vol. 118, pp. 2105-2106.

* cited by examiner

PREPARATION OF PARTIALLY HYDROGENATED RAC-ANSA-METALLOCENE COMPLEXES

The present invention relates to a process for preparing hydrogenated or partially hydrogenated, racemic ansa-metallocene complexes, to the complexes themselves and derivatives thereof and to their use as catalysts or as a constituent of catalysts for the polymerization of olefinically unsaturated compounds or as reagents or catalysts in stereoselective synthesis.

Apart from stereospecific olefin polymerization, enantioselective organic synthesis is increasingly offering interesting possible uses for chiral metallocene complexes of metals of transition groups III-VI of the Period Table of the Elements. The applications mentioned generally require the use of a metallocene complex in its racemic form, i.e. without meso compounds. In the case of the diastereomer mixture (rac and meso form) usually obtained in metallocene syntheses of the prior art, the meso form has to be separated off. There have therefore been attempts in the past to develop racemoselective syntheses of ansa-metallocenes, and corresponding synthetic routes of a general nature are described, for example, in WO 99/15538 and in DE 10030638. The racemoselective synthesis of ansa-metallocenes proceeds via the intermediate of an ansa-metallocene bisphenoxide or an ansa-metallocene biphenoxide.

Hydrogenated metallocenes such as ethylenebis(tetrahydroindenyl)zirconium dichloride and dimethylsilanediylbis(tetrahydroindenyl)zirconium dichloride are known from J. Am. Chem. Soc. (1996), 118, 2105, J. Mol. Katal. A. Chem. (1995), 102, 59, EPA 0643079 and JPA 07292019. They are suitable for the preparation of polyolefins such as isotactic polypropylene, copolymers and elastomers. In addition, a series of further, hydrogenated metallocenes are also known, cf. EPA 0581754, JPA 07041521. Hydrogentated and partically hydrogenated metallocenes have likewise been described as catalyst precursors for the polymerization of olefins, cf., for example, EPA 0344887, EPA 0185918 and EPA 0537686. Hydrogenated and partially hydrogenated metallocenes have a different three-dimensional structure and different polymerization properties compared to their unsaturated analogues, and this altered structure and properties leads to advantageous effects and possible uses in particular applications.

In the prior art, the preparation of hydrogenated or partially hydrogenated ansa-metallocenes, in particular those having partially hydrogenated indenyl systems as ligands, is usually carried out via preparation of the bisindenyl-zirconocene dichlorides, their isolation and subsequent hydrogenation, followed by isolation of the hydrogenated or partially hydrogenated product by crystallization (cf., for example, EP 839 822 and references cited therein). This synthetic route has a number of disadvantages:

The synthesis of the ansa-metallocene dichloride complexes is normally carried out via the general route using zirconium tetrachloride as metal source: here, the ansa-ligand is dissolved in toluene, deprotonated by means of strong bases and then reacted with zirconium tetrachloride to give the corresponding ansa-metallocene dichloride (plus two equivalents of lithium chloride). The ansa-metallocene dichloride, which mostly precipitates during its formation, is separated off from the lithium chloride by known methods and the complex is, if appropriate, purified further by crystallization.

This "classical" reaction route has two significant problems. Apart from the desired racemate, virtually equivalent quantities of the mirror-symmetric meso diastereomer are formed in most cases. In addition, the yields of rac/meso mixture achieved using this strategy are relatively low (in the order of from about 30 to 40%). However, when the ansa-metallocene dichlorides are to be employed as catalysts for the polymerization of substituted olefins, only the racemates can be used (as mentioned above). In terms of the ansa-metallocene dichloride synthesis, this requires an often laborious and disadvantageous rac/meso separation or even destruction of the meso complex. As a result of this, the final yield of pure rac-ansa-metallocene dichloride is usually not more than 15-20%.

Further disadvantages are associated with the efficiency of the synthesis. As described above, the ansa-metallocene dichloride has to be separated from the lithium chloride which is formed simultaneously. This step is often relatively difficult, since the separation of the sparingly soluble (particularly in toluene) ansa-metallocene dichloride from the likewise virtually insoluble (in toluene) lithium chloride requires large amounts of solvent and therefore limits the productivity and efficiency of the synthetic route.

Furthermore, owing to the low solubility of the ansa-metallocene dichloride in hydrocarbon solvents, the concentrations of the complex in the hydrogenation reaction of this complex are relatively low in most cases. This also restricts the productivity and efficiency of the overall synthetic route.

For this reason, partially hydrogenated ansa-metallocenes have hitherto only been obtainable if often considerable losses in yield and uneconomical synthesis conditions are accepted.

It is an object of the present invention to avoid the disadvantages of the prior art and provide a simple and cost-effective but at the same time highly effective process for preparing hydrogenated and partially hydrogenated, racemic metallocene complexes which are virtually free of meso isomer (NMR measurement accuracy). A particular object of the present invention is to find a racemoselective synthetic route to hydrogenated and/or partially hydrogenated metallocene complexes which leads in a simple and inexpensive manner to end products which can be isolated in pure form. A further object is to find hydrogenated or partially hydrogenated, racemic metallocene complexes which can either be used directly as catalysts, primarily for olefin polymerization, or be used after modification, for example after substitution of an "auxiliary ligand", as or in catalysts, primarily for olefin polymerization, or which can be used as reagents or catalysts in stereoselective synthesis.

We have found that this object is achieved by the process defined in the claims, the resulting hydrogenated or partially hyrogenated, racemic metallocene complexes (VI) and their use as catalysts or in catalysts for the polymerization of olefinically unsatura ted compounds or as reagents or catalysts in stereoselective synthesis.

The terms "meso form", "racemate" and thus also "enantiomers" in the context of metallocene complexes are known and defined, for example, in Rheingold et al., Organometallics 11 (1992), p. 1869-1876.

For the purposes of the present invention, the term "virtually meso-free" means that more than 80%, preferably at least 90%, of a compound are present in the form of the racemate, particularly preferably at least 95%.

In the present context, the term "hydrogenated or partially hydrogenated" means that at least one pair or a plurality of pairs of the unsaturated carbon atoms, i.e. $sp^2$-hybridized carbon atoms, present in the ligand system prior to the hydrogenation step are hydrogenated, i.e., are present after the hydrogenation in hydrogen-saturated form, namely as $sp^3$-hybridized carbon atoms.

The process of the present invention for preparing hydrogenated or partially hydrogenated, racemic ansa-metallocene complexes comprises the following seps:

reacting bridged or unbridged transition metal-aromatic complexes of the formula I

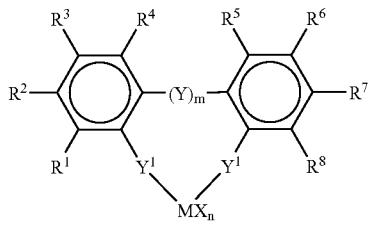

(I)

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, —$OR^{10}$ or —$NR^{10}R^{11}$, n is an integer from 1 to 4 and corresponds to the valence of M minus 2, $R^1$ to $R^8$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, where adjacent radicals from $R^2$ to $R^7$ may also form saturated, partially saturated or unsaturated cyclic groups having from 4 to 15 carbon atoms, $Si(R^9)_3$, —$OR^{10}$, —$SR^{10}$, —$N(R^{10})_2$, —$P(R^{10})_2$, and all the abovementioned radicals may be fully or partially substituted by heteroatoms, $R^9$ are identical or different and are each $C_1$-$C_{20}$-alkyl, $C_3$-$C_{10}$-cycloalkyl, $C_6$-$C_{15}$-aryl, where the radicals mentioned may be partially or fully substituted by heteroatoms, $R^{10}$ are identical or different and are each $C_1$-$C_{10}$-alkyl, $C_6$-$C_{15}$-aryl, $C_3$-$C_{10}$-cycloalkyl, alkylaryl or $Si(R^{11})_3$, $R^{11}$ are identical or different and are each $C_1$-$C_{10}$-alkyl, $C_6$-$C_{15}$-aryl, $C_3$-$C_{10}$-cycloalkyl, alkylaryl;

Y, $Y^1$ are identical or different and are each

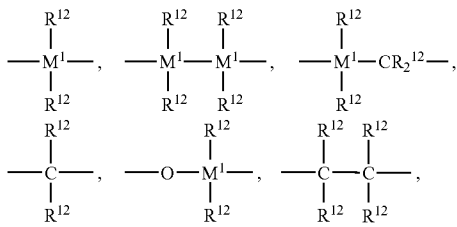

or =$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$-$C_{11}$alkyl, $C_1$-$C_{10}$-fluoroalkyl, $C_6$-$C_{10}$-fluoroaryl, $C_6$-$C_{10}$-aryl, $C_1$-$C_{10}$-alkoxy, $C_2$-$C_{10}$-alkenyl, $C_7$-$C_{40}$-arylalkyl, $C_8$-$C_{40}$-arylalkenyl, $C_7$-$C_{40}$-alkylaryl, or two radicals $R^{12}$ together with the atoms connecting them form a ring, $M^1$ is silicon, germanium or tin and m is 0, 1, 2 or 3, or Y is nonbridging and represents two radicals R' and R", where R', R" are as defined for $R^1$ to $R^8$ and R', R" together with adjacent radicals $R^4$, $R^5$ may also form saturated, partially saturated or unsaturated cyclic groups having from 4 to 15 carbon atoms, with cyclopentadienyl derivatives of the formula II

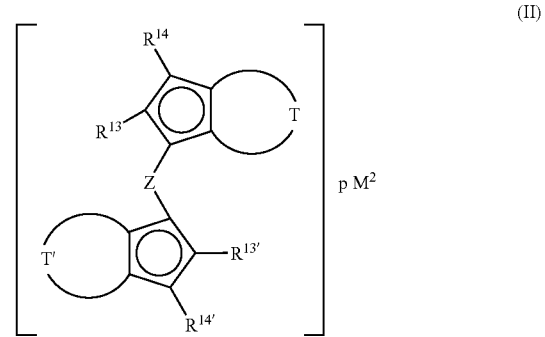

where

is a divalent group such as

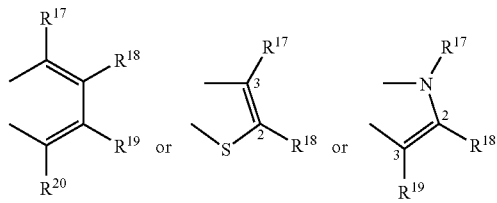

and

is a divalent group such as

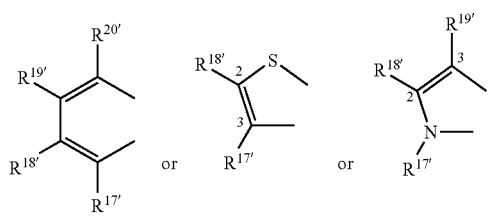

and the substituents and indices have the following meanings:

$R^{13}$, $R^{13'}$, $R^{14}$, $R^{14'}$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{10}$, —$SR^{10}$, —$N(R^{10})_2$, —$P(R^{10})_2$ or $Si(R^9)_3$, Z is a -$[Q(R^{15})(R^{16})]_q$— group, where Q may be identical or different and are each silicon, germanium, tin or carbon, $R^{15}$, $R^{16}$ are each hydrogen, $C_1$-$C_{10}$-alkyl, $C_3$-$C_{10}$-cycloalkyl or $C_6$-$C_{15}$-aryl, and q is 1, 2, 3 or 4;

$R^{17}$-$R^{20}$, $R^{17'}$-$R^{20'}$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl or arylalkyl, where adjacent radicals may together form cyclic groups having from 4 to 15 carbon atoms, or $Si(R^{11})_3$, and $M^2$ is an alkali metal ion or alkaline earth methal ion, and p is 1 when $M^2$ is an alkaline earth metal ion and is 2 when $M^2$ is an alkali metal ion;

and heating the resulting reaction mixture to a temperature in the range from minus 78° C. to 250° C., with or without addition of free radicals or free radical formers, to give a complex of the formula III

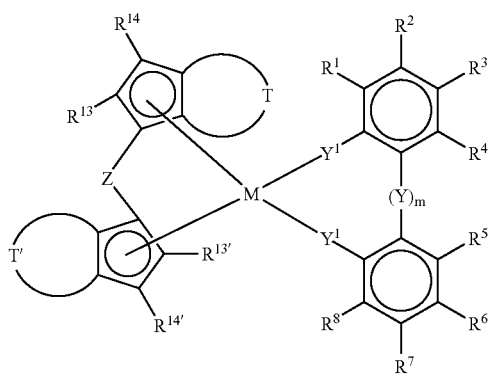

and at least partially hydrogenating III by means of hydrogen in the presence of a suitable catalyst.

It has surprisingly been found that the racemoselective synthesis of hydrogenated or partially hydrogenated metallocene complexes can be achieved successfully when transition metal complexes of the formula I are prepared, preferably without isolation of intermediates, from corresponding bridged biphenoxide-type or unbridged bisphenoxide-type ligands by reaction with transition metal halides in a manner known per se, these complexes are reacted with cyclopentadienyl derivatives of the formula II to give biphenoxide- or bisphenoxide-substituted metallocenes having aromatic bis-indenyl ligands, or heteroatom-containing analogues thereof, of the formula III which are subsequently catalytically hydrogenated in the reaction mixture. It has been found that this reaction route leads racemoselectively and in high yields to the corresponding hydrogenated or partially hydrogenated, racemic biphenoxide- or bisphenoxide-substituted ansa-metallocenes. In this way, a yield-reducing, complicated diastereomer separation is avoided.

The hydrogenated or partially hydrogenated, racemic biphenoxide- or bisphenoxide-substituted ansa-metallocenes can be used as catalysts either directly or after conversion into the corresponding partially hydrogenated ansa-metallocene dichloride complexes by replacement of the phenoxide ligands. Since the biphenoxide- or bisphenoxide-substituted ansa-metallocenes are, in contrast to the corresponding hydrogenated or partially hydrogenated ansa-metallocene dichloride complexes, relatively readily soluble in organic solvents, separating them from LiCl or other salts or the hydrogenation catalyst is considerably simpler. Furthermore, the synthesis can be carried out in highly concentrated solutions, which further improves the economics of this reaction route.

In the process of the present invention, preference is given to using bridged or unbridged transition metal-aromatic complexes of the formula I,

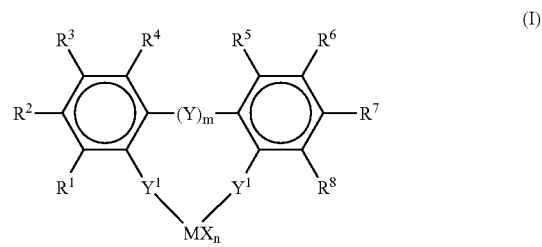

which are prepared in a manner known per se from compounds of the formula IV

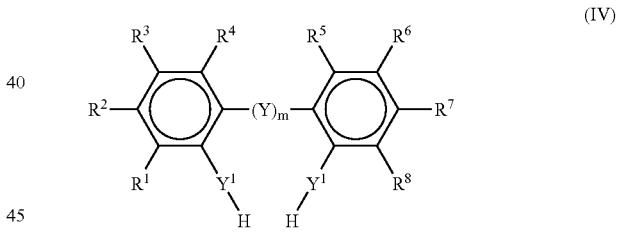

by deprotonation using suitable deprotonating agents and the subsequent reaction of the deprotonated compounds with a suitable transition metal compound of the formula V

$$MX_4(\text{Lewis base})_k \qquad (V)$$

where k is 0, 1 or 2, with the substituents and indices in the formulae (I), (V) and (IV) having the following meanings:

M is titanium, zirconium, hafnium, in particular zirconium; and

X are identical or different and are each fluorine, chlorine, bromine, iodine, preferably chlorine, or $C_1$-$C_6$-alkyl such as methyl, ethyl, n-propyl, isopropyl, n-butyl, sec-butyl, i-butyl, preferably tert-butyl, or alkoxide —$OR^9$ or amide —$N(R^9)_2$ where $R^9$ are identical or different and are each preferably $C_1$-$C_{10}$-alkyl, $C_6$-$C_{15}$-aryl, alkylaryl, arylalkyl, fluoroalkyl or fluoroaryl each having from 1 to 10 carbon atoms in the alkyl radical and from 6 to 20 carbon atoms in the aryl radical, for example methyl, ethyl, i-propyl, tert-butyl, phenyl, naphthyl, p-tolyl, benzyl, trifluoromethyl, pentafluorphenyl.

The substituents $R^1$ to $R^8$ are identical or different and are each preferably hydrogen, fluorine, chlorine, bromine, iodine, $C_1$-$C_{20}$-alkyl, —$OR^{10}$, —$SR^{10}$, —$N(R^{10})_2$, —$P(R^{10})_2$ or $Si(R^9)_3$, where $R^9$ and $R^{10}$ are identical or different and are each $C_1$-$C_{10}$-alkyl, $C_6$-$C_{15}$-aryl, $C_3$-$C_{10}$-cycloalkyl, alkylaryl.

Furthermore, the substituents $R^1$ to $R^8$ may each be 3- to 8-membered cycloalkyl which may in turn bear a $C_1$-$C_{10}$-alkyl radical such as methyl, ethyl or propyl as substituent. Examples of such cycloalkyl radicals are cyclopropyl, cyclopentyl, preferably cyclohexyl, norbornyl. In particular embodiments, $R^1$ to $R^8$ may also be $C_6$-$C_{15}$-aryl such as phenyl or naphthyl or alkylaryl having from 1 to 10 carbon atoms in the alkyl part and from 6 to 20 carbon atoms in the aryl part, e.g. p-tolyl; arylalkyl having from 1 to 10 carbon atoms in the alkyl part and from 6 to 20 carbon atoms in the aryl part, e.g. benzyl, neophyl; or triorganosilyl such as $Si(R^9)_3$, where $R^9$ are identical or different and are each $C_1$-$C_{20}$-alkyl, $C_3$-$C_{10}$-cycloalkyl, $C_6$-$C_{15}$-aryl, for example trimethylsilyl, tertbutyldimethylsilyl, triphenylsilyl. The radicals mentioned can of course also be partially or fully substituted by heteroatoms, for example by S—, N—, O— or halogen-containing structural elements. Examples of such substituted radicals $R^1$ to $R^8$ are the trifluoromethyl, pentafluoroethyl, heptafluoropropyl, heptafluoroisopropyl and pentafluorophenyl groups.

Preferred substituents $R^1$ and $R^8$ for bridging Y and $R^1$, $R'$, $R''$ and $R^8$ for nonbridging Y are, independently of one another, $C_1$-$C_{10}$-alkyl groups such as methyl, ethyl, n-propyl, isopropyl, n-butyl, sec-butyl, i-butyl, tert-butyl, preferably simply methyl. Particular preference is given to all substituents $R^1$, $R'$, $R''$ and $R^8$ for nonbridging Y being identical and each being methyl and the substituents $R^1$ and $R^8$ in the case of bridging Y being identical and each being tert-butyl groups.

In preferred embodiments, $R^1$, $R'$, $R''$ and $R^8$ for nonbridging Y are all methyl, particularly preferably with $Y^1$ being —O—, i.e. 2 molecules of 2,6-dimethylphenol are used as ligands in formula (IV). In addition, the use of 2,4,6-trimethylphenol and 2,4-di-tert-butylphenol is also preferred according to the present invention.

The substituents $R^3$ and $R^6$ can be varied within a wide range to alter the solubility of the metallocene complexes (III) and (VI) resulting from the process of the present invention and, according to the present invention, are identical or different and are each hydrogen, fluorine, chlorine, bromine, iodine, preferably chlorine, alkoxide —$OR^{10}$, thiolate —$SR^{10}$, amine —$N(R^{10})_2$, —$P(R^{10})_2$ or $Si(R^9)_3$, where $R^9$ and $R^{10}$ are identical or different and are each $C_1$-$C_{10}$-alkyl, $C_3$-$C_{10}$-cycloalkyl, in particular 3- to 8-membered cycloalkyl which may in turn bear a $C_1$-$C_{10}$-alkyl radical such as methyl, ethyl or propyl as substituent. Examples of such cycloalkyl radicals are cyclopropyl, cyclopentyl, preferably cyclohexyl, norbornyl. Furthermore, $R^9$ and $R^{10}$ may also be halogen-substituted alkyl or cycloalkyl radicals, for example trifluoromethyl, pentafluoroethyl, heptafluoropropyl or heptafluoroisopropyl.

A person skilled in the art will choose alkyl, cycloalkyl or aromatic substituents $R^3$ and $R^6$ to increase the solubility of the metallocene complexes in nonpolar solvents and will choose polar substituents $R^3$ and $R^6$, for example halogen, alkoxide, thiolate, amine and the like, to reduce the solubility of the complexes in nonpolar solvents.

In the latter case, $R^3$ and $R^6$ are preferably halogens such as chlorine or bromine, alkoxides —$OR^{10}$, thiolates —$SR^{10}$ or amines —$N(R^{10})_2$, where $R^{10}$ is methyl, ethyl, n-propyl, isopropyl, tert-butyl, cyclopropyl, cyclopentyl, cyclohexyl, norbornyl.

Very particular preference is given to $R^{10}$ being methyl. $R^3$ and $R^6$ in formula (I) are particularly preferably chlorine, bromine, methoxy, ethoxy, isopropyloxy, tert-butyloxy, cyclopropyloxy or cyclohexyloxy.

Variation of the substituents $R^3$ and $R^6$ over a wide range does not have an adverse effect on the racemoselectivity of the synthesis, so that appropriate choice of the substituents, taking account of the chosen reaction conditions, enables the yield of the synthesis to be increased and improved in a targeted manner.

For the purposes of the present invention, phehoxides, biphenoxides or bisphenoxides (or their analogous derivatives) are all compounds of the formula IV and their analogous derivatives claimed according to the present invention, i.e. both those particular compounds and ligands having this basic structure and other elements or groups as defined for $Y^1$ in place of the phenol oxygen in the position $Y^1$.

Apart from the abovementioned bridges Y and Y', preferred bridges in particular embodiments of the invention are methylene —$CH_2$—, —S—, —O—, —$C(CH_3)_2$—; very particular preference is given to the bridges $Y^1$ being identical and each being oxygen —O—. Furthermore, particular preference is given to biphenoxides in which m is zero and both $Y^1$ are oxygen.

When Y is nonbridging and represents two radicals $R'$ and $R''$, these are preferably defined as for $R^1$ to $R^8$, including the radicals indicated as preferred there. Furthermore, $R'$, $R''$ together with adjacent radicals $R^4$, $R^5$ can form saturated, partially saturated or unsaturated cyclic groups having from 4 to 15 carbon atoms.

Suitable deprotonating agents for the deprotonation of (IV) are, for example, n-butyllithium, tert-butyllithium, sodium hydride, potassium tert-butoxide, Grignard reagents derived from magnesium, magnesium compounds such as di-n-butylmagnesium, (n,s)-dibutylmagnesium or other suitable alkyl compounds of alkaline earth metals or alkali metals.

The bridged or unbridged transition metal complexes of the formula (I) are subsequently reacted with cyclopentadienyl derivatives of the formula (II):

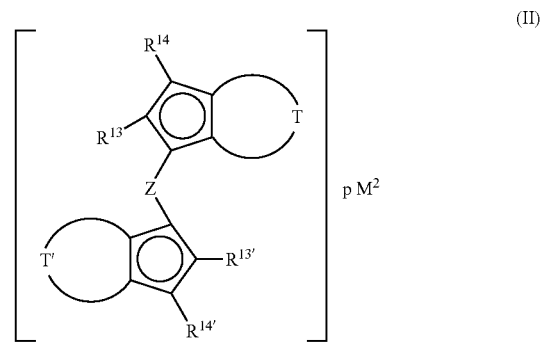

where the substituents and indices are as defined above, using methods which are generally known to those skilled in the art.

As cyclopentadienyl derivatives of the formula (II), preference is given to using those in which

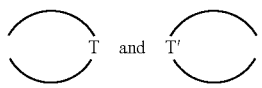

are

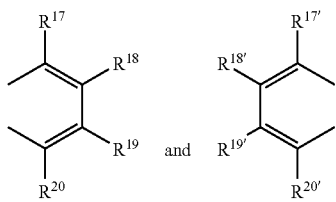

and in which $M^2$ is an alkali metal ion or an alkaline earth metal ion, in particular Li, Na, K, Rb, Cs, Be, Mg, Ca, Sr or Ba, where p=1 in the case of Be, Mg, Ca, Sr, Ba and p=2 in the case of Li, Na, K, Rb, Cs, with the radicals $R^{17}$ to $R^{20}$ and $R^{17'}$ to $R^{20'}$ being as defined above.

A well suited procedure has been found to be the following, which is generally carried out in the temperature range from −78 to 110° C., preferably initially at about 20° C., and in which the reaction may, if necessary, be completed by boiling under reflux.

The compounds of the formula (IV) are firstly deprotonated in a suitable solvent or solvent mixture, for example toluene or tetrahydrofuran (THF), by means of, for example, sodium hydride or n-butyllithium and the transition metal compound, for example the halide such as titanium tetrachloride, zirconium tetrachloride or hafnium tetrachloride, is subsequently added, advantageously in the form of the bis-THF adduct or the DME adduct of the formula (V). As an alternative, the deprotonated compound of the formula (IV) can be added to a solution of the transition metal compound. After the reaction is complete, the product (I) can generally be obtained by crystallization after salts have been separated off. However, preference is given to using the reaction mixture which has been freed of salts for the further procedure without isolation of (I).

The bridged or unbridged transition metal complexes (I) generally still contain from 1 to 4 equivalents of the Lewis base which is generally introduced via the synthetic route. Examples of such Lewis bases are ethers such as diethyl ether or tetrahydrofuran (THF) and also amines such as TMEDA. However, it is also possible to obtain the transition metal complexes (II) free of Lewis bases, for example by drying under reduced pressure or by choosing other solvents in the synthesis. Such measures are known to those skilled in the art.

The transition metal complexes of the formula (I) are reacted as described above with cyclopentadienyl derivatives of the formula (II), with or without subsequent heating of the reaction mixture obtained and in the presence or absence of free radicals or free radical formers, as described below.

Preference is given to using transition metal complexes (I) in which M is zirconium and the radicals $R^1$ to $R^8$ have the above-described preferred meanings and in which $Y^1$ are each oxygen. Very well suited complexes are dichlorozirconium bis(2,6-dimethylphenoxide), dichlorozirconium bis(2,4,6-trimethylphenoxide), dichlorozirconium bis(2,6-dimethyl-4-chlorophenoxide), dichlorozirconium bis(2,6-dimethyl-4-bromophenoxide), dichlorozirconium bis(2,6-dimethyl-4-methoxyphenoxide), dichlorozirconium bis(2,6-dimethyl-4-ethoxyphenoxide), dichlorozirconium bis(2,6-dimethyl-4-tert-butoxyphenoxide), dichlorozirconium bis(2,4-di-tert-butylphenoxide), dichlorozirconium bis(3,5-di-tert-butylphenoxide), dichlorozirconium 3,3'-di-tert-butyl-5,5'-dimethoxy-1,1'-bi-2-phenoxide, dichlorozirconium 3,3'-di-tert-butyl-5,5'-diethoxy-1,1'-bi-2-phenoxide, dichlorozirconium 3,3'-di-tert-butyl-5,5'-dipropyloxy-1,1'-bi-2-phenoxide, dichlorozirconium 3,3'-di-tert-butyl-5,5'-dimethylthio-1,1'-bi-2-phenoxide, dichlorozirconium 3,3'-di-tert-butyl-5,5'-diethylthio-1,1'-bi-2-phenoxide, dichlorozirconium 3,3'-di-tert-butyl-5,5'-dipropylthio-1,1'-bi-2-phenoxide, their solvent adducts and the zirconium bisphenoxide and zirconium biphenoxide compounds mentioned in the examples.

The reaction according to the present invention of compounds of the formula (I) with cyclopentadienyl derivatives of the formula (II) in the process of the present invention leads initially in a known manner to the transition metal complexes of the formula (III)

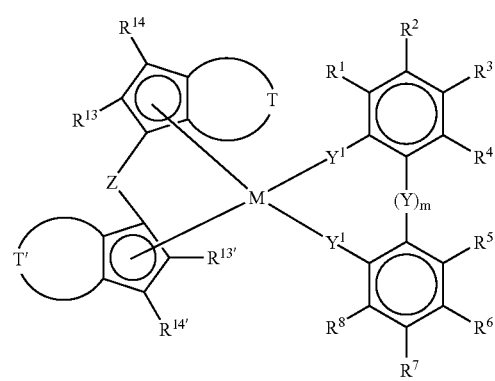

(III)

where all substituents are as defined above, including the preferred substituents.

In a further process step, the complexes of the formula (III) are at least partially hydrogenated in the presence of a suitable catalyst to give hydrogenated or partially hydrogenated, racemic ansa-metallocene complexes of the formula (VI):

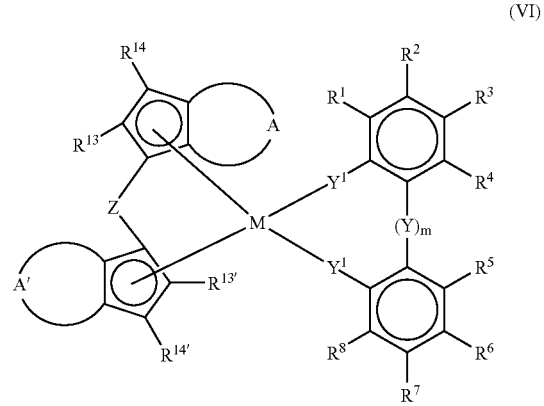

(VI)

where the substituents and indices have the abovementioned meanings, in particular the preferred meanings, and:

is a divalent group such as

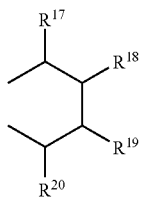 or 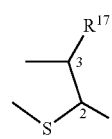 or 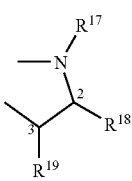

and

is a divalent group such as

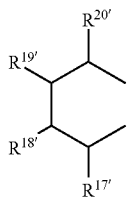 or 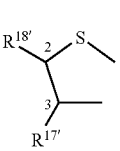 or 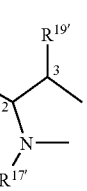

where:

$R^{13}$, $R^{13'}$, $R^{14}$, $R^{14'}$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —$OR^{10}$, —$SR^{10}$, —$N(R^{10})_2$, —$P(R^{10})_2$ or $Si(R^9)_3$, and Z is a -$[Q(R^{15})(R^{16})]_q$-group, where Q can be identical or different and is silicon, germanium, tin or carbon, $R^{15}$, $R^{16}$ are each hydrogen, $C_1$-$C_{10}$-alkyl, $C_3$-$C_{10}$-cycloalkyl or $C_6$-$C_{15}$-aryl, and q is 1, 2, 3 or 4;

$R^{17}$-$R^{20}$, $R^{17'}$-$R^{20'}$ are identical or different and are each hydrogen, $C_1$-$C_{20}$-alkyl, 3- to 8-membered cycloalkyl which may in turn bear a $C_1$-$C_{10}$-alkyl group as substituent, $C_6$-$C_{15}$-aryl or arylalkyl, where adjacent radicals may also together form cyclic groups having from 4 to 15 carbon atoms, or $Si(R^{11})_3$.

Particular preference is given to

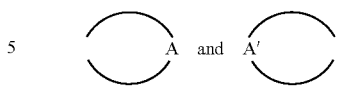

being

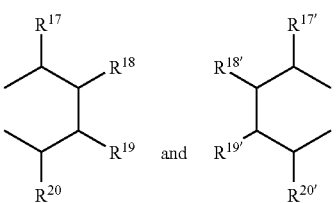

where $R^{17}$-$R^{20}$, $R^{17'}$-$R^{20'}$ are identical or different and are each preferably hydrogen, $C_1$-$C_{10}$-alkyl, where adjacent radicals may together also form cyclic groups having from 4 to 15 carbon atoms.

The hydrogenation can be carried out in the presence of a homogeneous or heterogeneous catalyst, preferably a heterogeneous catalyst. Suitable catalysts are Pt, Pd, Rh, Ru, Os and also nikkel, Raney nickel, their oxides, salts or complexes, mixtures thereof, if desired on suitable catalyst supports. Particular preference is given to carrying out the hydrogenation in the presence of heterogeneous palladium catalysts, in particular palladium on carbon or activated carbon.

Further examples of hydrogenation catalysts which are suitable for the purposes of the present invention are palladium on barium sulfate, palladium on aluminum oxide, palladium black, palladium sponge, platinum oxide, platinum black, platinum sponge, platinum dioxide, etc.

Suitable hydrogenation catalysts are in principle those compounds or elements which do not hydrogenate or only partly hydrogenate the solvent under the hydrogenation conditions employed.

The catalytic hydrogenation is preferably carried out in the temperature range from 0° C. to 150° C., in particular in the range from 15° C. to 100° C. The solvents used in the reaction are suitable hydrogenation-stable solvents, particularly preferably halogen-free solvents. Solvents which are suitable for this purpose are aromatic solvents such as benzene, toluene, xylene (as an isomer mixture), o-xylene, m-xylene, p-xylene, mesitylene, tetralin, anisole, cumene, 1,2-diethylbenzene, 1,3-diethylbenzene, 1,4-diethylbenzene, 1-ethyl-2-methylbenzene, 1-ethyl-3-methylbenzene, 1-ethyl-4-methylbenzene. Preference is given to anisole, toluene, benzene, xylenes (as a mixture or pure substances) and tetralin.

Further suitable solvents are aromatic or aliphatic ethers such as anisole, ethyl phenyl ether, isopropyl phenyl ether, diethyl ether, di-n-butyl ether, tert-butyl methyl ether, tetrahydrofuran, dioxane and dimethoxyethane (DME). It is also possible to use esters of aliphatic or aromatic carboxylic acids as solvents, for example ethyl acetate and propyl butyrate.

Furthermore, it is also possible to use halogenated solvents such as dichloromethane. However, preference is given to using nonhalogenated solvents since the use of halogenated solvents in relatively large quantities is only possible when strict safety and environmental regulations are adhered to. In addition, only hydrogenation catalysts having a low activity, e.g. platinum black or platinum dioxide, can be used in chlorinated solvents if halogenation reactions are to be avoided.

The halogenation reactions lead to decomposition of the product and to corrosion problems in the apparatuses used.

The heterogeneously catalyzed hydrogenation in the process of the present invention is generally carried out in appropriate pressure vessels, i.e. autoclaves, which are pressurized with hydrogen gas ($H_2$). Suitable hydrogen pressures are in the range up to 100 bar, preferably up to 30 bar, particularly preferably up to 20 bar.

The racemic metallocene complexes of the formula (VI) which have been hydrogenated or partially hydrogenated according to the present invention can be used either directly as catalysts or as constituents of catalysts for the polymerization of olefinically unsaturated compounds or as reagents or catalysts in stereoselective synthesis, or can generally be modified further.

In particular, one or both of the phenoxide ligands or the single biphenoxide ligand in the complex (VI) can, for example, be replaced by substitution before further use. Suitable substitution methods are reaction of the racemic metallocene complexes of the formula (VI) with $SOCl_2$, silicon tetrachloride, methylaluminum dichloride, dimethylaluminum chloride, aluminum trichloride, dialkylaluminum chlorides, aluminum sesquichlorides, particularly preferably ethylaluminum dichloride, or a Brönsted acid such as hydrogen halide, i.e. HF, HBr, HI, preferably HCl, which is generally used as such or as a solution in water or an organic solvent such as diethyl ether or THF. Well-suited solvents are aliphatic hydrocarbons such as pentane, hexane, heptane, aromatic hydrocarbons such as toluene, ortho-, meta- or para-xylene or isopropylbenzene (cumene), ethers such as tetrahydrofuran (THF); diethyl ether, methyl tert-butyl ether or dimethoxyethane (DME), amines such as diisopropylamine, tetramethylethanediamine (TMEDA) or pyridine.

Also suitable are Lewis-base-containing solvent mixtures comprising hydrocarbons and ethers or amines or both, for example mixtures of toluene and THF, toluene and DME or toluene and TMEDA, with the Lewis base generally being present in an amount of 0.01-50 mol %, preferably 0.1-10 mol %, based on the solvent mixture. Particularly useful substitution reagents are carboxylic acid halides such as acetyl chloride, phenylacetyl chloride, 2-thiophenacetyl chloride, trichloroacetyl chloride, trimethylacetyl chloride, O-acetylmandelyl chloride, 1,3,5-benzenetricarboxylic chloride, 2,6-pyridinecarboxylic chloride, tert-butylacetyl chloride, chloroacetyl chloride, 4-chlorophenylacetyl chloride, dichloroacetyl chloride, 3-methoxyphenylacetyl chloride, acetyl bromide, bromoacetyl bromide, acetyl fluoride, benzoyl fluoride, with these generally being used in the above-mentioned solvents or as such.

This usually gives the analogous monohalide or dihalide of the formula (VIa)

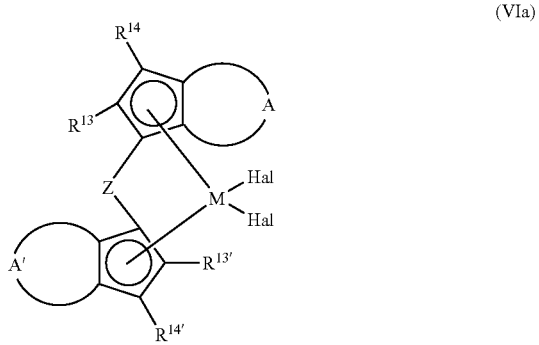

(VIa)

where Hal is fluorine, chlorine, bromine or iodine.

Preferred metallocenes of the formula VIa which can be prepared by the process of the present invention are, without being restricted thereto:
rac-dimethylsilanediylbis(4,5,6,7-tetrahydroindenyl)zirconium dichloride,
rac-dimethylsilanediylbis(2-methyl-4,5,6,7-tetrahydroindenyl)zirconium dichloride,
rac-dimethylsilanediylbis(2-4,5,6,7-tetrahydromethylindenyl)zirconium dibromide,
rac-dimethylsilanediylbis(2-methyl-4-phenyl-4,5,6,7-tetrahydroindenyl)zirconium dichloride,
rac-dimethylsilanediylbis[2-methyl-4-(1-naphthyl)-4,5,6,7-tetrahydroindenyl]zirconium dichloride,
rac-dimethylsilanediylbis[2-methyl-4-(1-naphthyl)-4,5,6,7-tetrahydroindenyl]hafnium dichloride,
rac-dimethylsilanediylbis(2-methyl-6,7-dihydro-4,5-benzoindenyl)zirconium dichloride, dichloride,
rac-dimethylsilanediylbis(2-methyl-4,6-diisopropyl-4,5,617-tetrahydroindenyl)zirconium dichloride,
rac-dimethylsilanediylbis(2-methyl-4,6-diisopropyl-4,5,6,7-tetrahydroindenyl)zirconium difluoride,
rac-dimethylsilanediylbis(2-ethyl-4,5,6,7-tetrahydroindenyl)zirconium dichloride,
rac-dimethylsilanediylbis(2-ethyl-4-phenyl-4,5,6,7-tetrahydroindenyl)zirconium dichloride,
rac-dimethylsilanediylbis(2-ethyl-4-phenyl-4,5,6,7-tetrahydroindenyl)hafnium dichloride,
rac-dimethylsilanediylbis[2-ethyl-4-(1-naphthyl)-4,5,6,7-tetrahydroindenyl]zirconium dichloride,
rac-dimethylsilanediylbis(2-ethyl-6,7-dihydro-4,5-benzoindenyl)zirconium dichloride,
rac-dimethylsilanediylbis(4,5-benzo-4,5,6,7-tetrahydroindenyl)zirconium dichloride,
rac-dimethylsilanediylbis(2-ethyl-4,6-diisopropyl-4,5,6,7-tetrahydroindenyl)zirconium dichloride,
rac-dimethylsilanediylbis(2-ethyl-4,6-dimethyl-4,5,6,7-tetrahydroindenyl)zirconium dichloride,
rac-dimethylsilanediylbis(2,4,6-trimethyl-4,5,6,7-tetrahydroindenyl)hafnium dichloride,
rac-isopropylidenebis(4,5,6,7-tetrahydroindenyl)zirconium dichloride
rac-ethanediylbis(4,5,6,7-tetrahydroindenyl)zirconium difluoride,
rac-ethanediylbis(4,5,6,7-tetrahydroindenyl)zirconium dichloride,
rac-ethanediylbis(4,5,6,7-tetrahydroindenyl)zirconium dibromide,
rac-ethanediylbis(2-methyl-4,5,6,7-tetrahydroindenyl)zirconium dichloride,
rac-ethanediylbis(2-ethyl-4,5,6,7-tetrahydroindenyl)zirconium dichloride,
rac-ethanediylbis(2-ethyl-4,6-diisopropyl-4,5,6,7-tetrahydroindenyl)zirconium dichloride,
rac-ethanediylbis(2-methyl-6,7-dihydro-4,5-benzoindenyl)zirconium dichloride,
rac-ethanediylbis(2-ethyl-6,7-dihydro-4,5-benzoindenyl)zirconium dichloride,
rac-ethanediylbis(2-ethyl-4,5,6,7-tetrahydroindenyl)zirconium dichloride,
rac-ethanediylbis(2-ethyl-4-phenyl-4,5,6,7-tetrahydroindenyl)zirconium dichloride,
rac-ethahediylbisbis(2-ethyl-4-phenyl-4,5,6,7-tetrahydroindenyl)hafnium dichloride,
rac-ethanediylbis[2-ethyl-4-(1-naphthyl)-4,5,6,7-tetrahydroindenyl]zirconium dichloride, and also the compounds mentioned in the examples.

A further well-suited substitution method is reaction of the hydrogenated or partially hydrogenated, racemic metallocene complexes of the formula (VI) with organoaluminum compounds such as tri-$C_1$-$C_{10}$-alkylaluminum, i.e. trimethylaluminum, triethylaluminum, tri-n-butylaluminum, triisobutylaluminum. On the basis of the present state of knowledge, this generally forms the organo compound analogous to (VI) (organic radicals in place of the bi(s)phenoxide, e.g. $C_1$-$C_{10}$-alkyl such as methyl, ethyl, n-butyl, i-butyl) and, for example, the organoaluminum binaphthoxide.

In the substitution reactions, the components are usually used in a stoichiometric ratio, which depends on whether a monosubstituted or disubstituted product is to be obtained.

In particularly preferred embodiments, rac-ethanediylbis (4,5,6,7-tetrahydroindenyl)zirconium dichloride is prepared in the process of the present invention by reacting a dihalozirconium bis(2,4,6-trimethylphenoxide) compound or a dihalozirconium bis(2,6-dimethylphenoxide) compound or a dihalozirconium bis(2,4-di-tert-butylphenoxide) compound with ethane-1,2-diylbisindenyldilithium to form ethanediyl-bis(indenyl)zirconium bis(2,4,6-trimethylphenoxide) or ethanediylbis(indenyl)zirconium bis(2,4-dimethylphenoxide) or ethanediylbis(indenyl)zirconium bis(2,4-di-tert-butylphenoxide) which is subsequently hydrogenated to ethanediylbis(4,5,6,7-tetrahydroindenyl)zirconium bis(2,4,6-trimethylphenoxide) or ethanediylbis(4,5,6,7-tetrahydroindenyl)zirconium bis(2,4-dimethylphenoxide) or ethanediylbis(4,5,6,7-tetrahydroindenyl)zirconium bis(2,4-di-tert-butylphenoxide), and subsequently replacing the phenoxide groups.

The process of the present invention makes it possible to obtain the rac form of the metallocene complexes (III), and also the hydrogenated or partially hydrogenated complexes (VI) obtainable therefrom and the corresponding dihalides (VIa) obtainable there from and analogous compounds, very selectively.

The hydrogenated or partially hydrogenated, racemic metallocene complexes (VI) and downstream compounds can be obtained selectively and in high yields by the present novel process. Furthermore, the process of the present invention makes it possible for the solubility of the resulting products to be controlled in a simple fashion by selection of suitable substituents on the phenoxide or biphenoxide ligands, which makes isolation of the products easier and increases the yields of the synthesis. The good solubility of the complexes (III) to be hydrogenated in nonpolar solvents also makes it possible to work in concentrated solutions, which significantly improves the economics and efficiency of the synthesis described compared to the processes of the prior art.

A further significant advantage is that the process of the present invention can be carried out racemoselectively in a single-vessel process. For the purposes of the present invention, a single-vessel process means that no intermediates are isolated after the individual process steps. The further reaction can be carried out directly using the reaction product mixture from the preceding step.

The hydrogenated or partially hydrogenated racemic metallocene complexes obtained according to the present invention, in particular those of the formula (VI) or their above-described derivatives of the formula (VIa) which are obtainable, for example, by replacement of the (bi)phenoxide ligands, can be used as catalysts or in catalyst systems for the polymerization of olefinically unsaturated compounds such as ethylene, propylene, 1-butene, 1-hexene, 1-octene, styrene. They are particularly advantageous in the stereoselective polymerization of prochiral, olefinically unsaturated compounds such as propylene, styrene. Suitable catalysts or catalyst systems in which the racemic metallocene complexes obtainable according to the present invention can function as "metallocene component" are usually obtained by means of compounds which form metallocenium ions, for example as described in EP-A-0 700 935, page 7, line 34, to page 8, line 21, and the formulae (IV) and (V) therein. Further compounds capable of forming metallocenium ions are aluminoxanes $(RAlO)_n$ such as methylaluminoxane, or else boron activators.

The racemic metallocene complexes obtained according to the present invention, in particular those of the formula (VI) or their above-described derivatives of the formula (VIa) which can be obtained by, for example, replacement of the (bi)phenoxide ligands, can also be used as reagents or as catalysts or in catalyst systems in stereoselective synthesis, in particular stereoselective organic synthesis. Examples which may be mentioned are the stereoselective reduction or stereoselective alkylation of C=C double bonds or C=O— and C=N double bonds.

EXAMPLES

General procedures: Preparation and handling of the organometallic compounds were carried out in the absence of air and moisture under argon (Schlenk technique or glove box). All solvents required were purged with argon and dried over molecular sieves before use.

The solvents and reagents used in the examples were obtained commercially, for example:

| | |
|---|---|
| toluene | analytical reagent, Merck; |
| THF | 99.9%, anhydrous, from Acros; |
| n-butyllithium | 20% by weight in toluene, from Chemmetall; |
| biphenol | 99%+, from Aldrich |
| $ZrCl_4$ | 98%, from Cezus Chemie; |
| 2,4,6-trimethylphenol | 97%, from Aldrich. |

The preparation of the bridged bisindenyl ligands was carried out by customary methods known to those skilled in the art from the prior art; some of the bisindenyls used are also commercially available compounds. The BuLi solution used had a concentration of about 20% by weight of butyllithium in toluene (about 2.6 molar).

Example 1A

Preparation of ethanediylbis(4,5,6,7-tetrahydroindenyl)zirconium bis(2,4,6-trimethylphenoxide)

a) Preparation of $ZrCl_4$(DME)

In a dry 500 ml three-neck round-bottom flask which had been flushed with inert gas and was equipped with a magnetic stirrer bar, a dropping funnel and a vacuum connection with stopcock, 10.6 g (45.47 mmol) of zirconium tetrachloride were suspended in 50 g of toluene. The suspension was cooled to about 4° C. in an ice bath, after which 4.2 g of DME were slowly added via the dropping funnel over a period of 15 minutes. The suspension was allowed to warm to room temperature and was stirred for another hour.

b) Preparation of Li(2,4,6-$Me_3$-$C_6H_2O$)

In a dry 500 ml three-neck round-bottom flask which had been flushed with inert gas and was equipped with a magnetic stirrer rod, dropping funnel and vacuum connection with stopcock, 12.8 g (91 mmol) of 2,4,6-trimethylphenol were dissolved in 50 g of toluene and 8.4 g of DME. The solution was cooled to about 4° C. in an ice bath, after which 28.3 g of a BuLi solution (20% by weight) were added via the dropping funnel over a period of 15 minutes. After the addition was complete, the solution was allowed to come to room temperature and was stirred for another hour at room temperature.

c) Preparation of $(DME)Cl_2Zr(2,4,6-Me_3-C_6H_2O)_2$

The solution from step b) was added via a syringe over a period of a number of minutes to the suspension from step a) at room temperature under nitrogen. Residual lithium phenoxide remaining in the round-bottom flask were rinsed out using 10 ml of toluene.

d) Preparation of ethane-1,2-diylbisindenyldilithium

In a dry 1000 ml three-neck round-bottom flask which had been flushed with inert gas and was equipped with magnetic stirrer bar, dropping funnel and vacuum connection with stopcock, 9.80 g (37.9 mmol) of 1,2-ethanediylbisindenyl were dissolved in 50 g of toluene and 8.4 g of DME. At room temperature, 25.6 g of a BuLi solution (20% by weight) were slowly added dropwise over a period of 20 minutes. The resulting suspension was stirred for a further 2.5 hours at room temperature.

e) Preparation of ethanediylbis(indenyl)zirconium bis(2,4,6-trimethylphenoxide)

The suspension from step c) was added via a syringe to the suspension from step d) under nitrogen. Residues remaining in the round-bottom flask were rinsed out using 10 ml of toluene. The combined suspension was stirred overnight at room temperature and subsequently heated to 60° C. and placed by means of a syringe under nitrogen on a glass filter frit No. 4 which had been flushed with inert gas. The suspension was filtered into a 1000 ml round-bottom flask with stopcock and the filter cake was washed with 10 g of toluene.

f) Synthesis of ethanediylbis(4,5,6,7-tetrahydroindenyl)zirconium bis(2,4,6-trimethylphenoxide) by hydrogenation The solution obtained in step e) was transferred under nitrogen into a 1000 ml autoclave provided with a hydrogen connection. 2.3 g of palladium on carbon and 2.8 g of $NHEt_2$ were added to this solution. The stirrer was started and the reactor was flushed three times with nitrogen and subsequently three times with hydrogen. The reactor was heated to 60° C. and pressured with 20 bar of $H_2$. After two hours, the pressure had dropped to about 17 bar and was increased again to 20 bar. After 4.5 hours, the pressure had dropped to 19 bar and was again brought back to 20 bar. Stirring and heating were stopped and the reactor was allowed to stand overnight. After 12 hours, the hydrogen pressure had dropped to 17 bar and was once again increased to 20 bar. The NMR spectrum indicated incomplete reaction. 2.5 mol % of Pd/C were added as a suspension in 30 g of toluene. The reactor was again heated to 60° C. for four hours, with no hydrogen being consumed. 10.9 mol % of Pd/C were added as a suspension in 50 g of toluene. After 19 hours without stirring and heating, the hydrogen pressure had dropped to 18 bar. The reactor was again heated to 60° C. and after 2.5 hours was cooled to room temperature. The resulting solution was filtered. The filtrate had a mass of 353 g. The $^1$H-NMR spectrum showed complete hydrogenation of the starting compound to the target complex.

The filtrate was subsequently divided into two parts. Part two had a mass of 172.5 g and contained approximately 20 mmol of the hydrogenated target complex ethanediylbis(4,5,6,7-tetrahydroindenyl)zirconium bis(2,4,6-trimethylphenoxide).

Example 1B

Preparation of ethanediylbis(4,5,6,7-tetrahydroindenyl)zirconium dichloride 3.5 g of acetyl chloride in 10 g of toluene were slowly added at room temperature via a dropping funnel to 172.5 g of the solution obtained in Example 1A. A precipitate formed during the addition of the solution. The mixture was then allowed to stand for five hours at room temperature. 0.8 g of acetyl chloride in 5 g of toluene was subsequently added via the dropping funnel. The $^1$H-NMR spectrum showed no resonance which could be assigned to the starting complex (bisphenoxide). The suspension was allowed to stand overnight and was subsequently filtered. The filter cake was dried under reduced pressure and had a mass of 3 g. The $^1$H-NMR spectrum indicated purely racemic ethanediylbis(4,5,6,7-tetrahydro-indenyl)zirconium dichloride. The total yield is about 35%. The filtrate had a mass of 188.7 g.

The filtrate was subsequently concentrated to 21.7 g, with a small quantity of precipitate forming. Small quantities of heptane were added, but no further precipitate was formed. The total yield from Example 1A plus Example 1B: 35%.

Example 2

Improved preparation of ethanediylbis(4,5,6,7-tetrahydroindenyl)zirconium bis(2,4,6-trimethylphenoxide) and ethanediylbis(4,5,6,7-tetrahydroindenyl)zirconium dichloride a) Preparation of $ZrCl_4(THF)_2$ In a dry 500 ml three-neck round-bottom flask which had been flushed with inert gas and was equipped with magnetic stirrer rod, dropping funnel and vacuum connection with stopcock, 10.6 g (45.47 mmol) of $ZrCl_4$ were suspended in 50 g of toluene. The suspension was cooled to approximately 4° C. in an ice bath, after which 6.9 g of THF were slowly added via the dropping funnel over a period of 15 minutes. The suspension was allowed to warm to room temperature and was stirred for another 40 minutes.

b) Preparation of $Li(2,4,6-Me_3-C_6H_2O)$

In a dry 500 ml three-neck round-bottom flask which had been flushed with inert gas and was equipped with magnetic stirrer rod, dropping funnel and vacuum connection with stopcock, 12.8 g of 2,4,6-trimethylphenol (91 mmol) were dissolved in 50 g of toluene and 6.6 g of THF. The solution was cooled to about 4° C. in an ice bath and 28.3 g of a 20% strength by weight BuLi solution were subsequently added dropwise via the dropping funnel over a period of 15 minutes. After the addition was complete, the mixture was allowed to warm to room temperature and was stirred for another 40 minutes.

c) Preparation of $(THF)_2Cl_2Zr(2,4,6-Me_3-C_6H_2O)_2$

The solution from step b) was added under nitrogen by means of a syringe to the suspension from step a) at room temperature over a period of several minutes and the resulting suspension was stirred for a further 2.5 hours at room temperature.

d) Preparation of ethane-1,2-diylbisindenyldilithium

In a dry 1000 ml three-neck round-bottom flask which had been flushed with inert gas and was equipped with a magnetic stirrer rod, a dropping funnel and vacuum connection with stopcock, 9.8 g (37.9 mmol) of 1,2-ethandiylbisindenyl were dissolved in 50 g of toluene and 3.9 g of THF. At room temperature, 25.6 g of a 20% strength by weight BuLi solution were slowly added dropwise over a period of 20 minutes. The suspension was stirred for a further 2.5 hours at room temperature.

e) Preparation of ethanediylbis(indenyl)zirconium bis(2,4,6-trimethylphenoxide)

The suspension obtained in step c) was added under nitrogen by means of a syringe to the suspension from step d). The suspension was stirred for 48 hours at room temperature and subsequently placed under nitrogen by means of a syringe on a glass filter frit No. 4 which had been flushed with inert gas. The suspension was filtered into a 1000 ml round-bottom flask with stopcock.

f) Synthesis of ethanediylbis(4,5,6,7-tetrahydroindenyl)zirconium bis(2,4,6-trimethylphenoxide) by hydrogenation The suspension obtained in step e) was transferred under nitrogen into a 1000 ml autoclave provided with a hydrogen connection. 2.3 g of palladium on carbon and 7.7 g of triethylamine were added to this solution. The stirrer was started and the reactor was flushed three times with nitrogen and then three times with hydrogen. The reactor was heated to 80° C. and subsequently pressurized with 20 bar of hydrogen. After 2.5 hours, the pressure had dropped to about 17.5 bar. An NMR spectrum showed complete hydrogenation of the starting compound. Stirring and heating were stopped, and the reactor was cooled to room temperature over a period four hours. To separate off the hydrogenation catalyst, the suspension was filtered through a Seitz filter. The filtrate had a mass of 290 g and was concentrated to 131.5 g at 50° C. and 150-200 mbar.

g) Preparation of ethanediylbis(4,5,6,7-tetrahydroindenyl) zirconium dichloride 7.5 g of acetyl chloride in 50 g of toluene were added dropwise at room temperature via a dropping funnel to the solution obtained in step f). During the addition of the acetyl chloride solution, a precipitate formed. After all of the acetyl chloride solution had been added, the suspension was allowed to stand at room temperature for four hours. During this time, a dense precipitate formed. The reaction mixture was warmed at 30° C. without the precipitate dissolving. The reaction mixture was stirred at room temperature for a further 48 hours. 30 g of heptane were then added to the solution. The precipitate which formed was filtered off and washed three times with 20 g of heptane and once with 10 g of heptane. The precipitate was dried under reduced pressure for a number of hours and had a final mass of 8.3 g. A $^1$H-NMR spectrum showed that the precipitate which had been filtered off consisted of pure rac-ethanediylbis(4,5,6,7-tetrahydroindenyl) zirconium dichloride. Total yield: 50% (based on amount of ligand).

Example 3

Synthesis of ethanediylbis(4,5,6,7-tetrahydroindenyl)zirconium bis(2,4,6-trimethylphenoxide) and ethanediylbis(4,5,6,7-tetrahydroindenyl)zirconium dichloride in a large batch a) Preparation of $ZrCl_4(THF)_2$ The preparation was carried out as in step a) of Example 2, but the amounts used were 46.6 g of $ZrCl_4$ (199.97 mmol), 219.8 g of toluene and 30.3 g of THF.

b) Preparation of $Li(2,4,6-Me_3-C_6H_2O)$

The preparation was carried out as in step b) of Example 2, but the amounts used were 56.3 g of 2,4,6-trimethylphenol (413.3 mmol), 220 g of toluene, 29 g of THF and 124.3 g of a 20% strength BuLi solution.

c) Preparation of $(THF)_2Cl_2Zr(2,4,6-Me_3-C_6H_2O)_2$

The preparation was carried out as in step c) of Example 2.

d) Preparation of ethane-1,2-diylbisindenyldilithium

The preparation was carried out as in step d) of Example 2 but the amounts used were 43.1 g of 1,2-ethanediylbisindenyl (166.82 mmol) in 220 g of toluene and 17.1 g of THF. 112.5 g of a 20% strength BuLi solution were added dropwise.

e) Preparation of ethanediylbis(indenyl)zirconium bis(2,4,6-trimethylphenoxide)

The preparation was carried out as described in step e) of Example 2 by combining the suspensions from steps c) and d). Residues which remained were washed out with 10 ml of toluene. The suspension was stirred for two hours at room temperature and filtered under nitrogen through a glass filter frit No. 4; the filter cake was washed with 50 g of toluene. The total mass of the filtrate was 1097.4 g, and the mass of the filter cake was 31 g. The filtrate was divided into three parts.

f1) Synthesis of ethanediylbis(4,5,6,7-tetrahydroindenyl)zirconium bis(2,4,6-trimethylphenoxide) by hydrogenation in the presence of triethylamine 274.35 g (theoretically 41.8 mmol) of the filtrate solution obtained in step e) were transferred under nitrogen to a 1000 ml autoclave provided with a nitrogen connection. 8.5 g of triethylamine were added to this solution, followed by 2.5 g of palladium on carbon. The stirrer was switched on and the reactor was flushed three times with nitrogen and then three times with hydrogen. The reactor was subsequently heated to 80° C. and pressurized with 20 bar of hydrogen. After 40 minutes, the hydrogen pressure had dropped to 18 bar and was brought back to 20 bar. After a further two hours, the pressure was still 20 bar. The NMR spectrum showed complete hydrogenation to the desired compound. The reactor was allowed to cool over a period of 1.5 hours and the suspension was transferred to a round-bottom flask; the reactor was rinsed out with 20 g of toluene. To separate off the hydrogenation catalyst, the suspension was filtered through a Seitz filter and the filter was washed with 20 g of toluene. The filtrate had a mass of 390.8 g.

g1) Synthesis of ethanediylbis(4,5,6,7-tetrahydroindenyl)zirconium dichloride 3.3 g of acetyl chloride in 10 ml of toluene were added dropwise at room temperature via the dropping funnel to the solution obtained in reaction step f1). During the addition, a precipitate formed. After the addition, the suspension was allowed to stand at room temperature for one hour. A further 3.3 g of acetyl chloride in 10 ml of toluene were then added dropwise. The reaction mixture was allowed to stand at room temperature for 12 hours. The reaction mixture was subsequently heated at 40° C. for five hours and then allowed to stand at room temperature for 72 hours. A further 1.8 g of acetyl chloride in 10 ml of toluene were then added and the mixture was stirred at room temperature for a total of. 17 hours. The reaction mixture was then heated at 45° C. for four hours and subsequently stirred at room temperature for another 96 hours. The mixture was then concentrated and 100 ml were distilled. The mixture was filtered through a filter No. 3 and the filter cake was washed with 15 g of toluene. The filter cake was dried under reduced pressure for a number of hours and had a mass of 11.4 g. The $^1$H-NMR spectrum showed purely racemic ethanediylbis(4,5,6,7-tetrahydroindenyl)zirconium dichloride.

The filtrate was concentrated to 260 g and stored at −20° C. for 12 hours. The precipitate which formed was filtered off and the filter cake was washed with small amounts of toluene. The precipitate was dried under reduced pressure and gave a further 1.7 g. The $^1$H-NMR spectrum showed a purely racemic product. The filtrate had a mass of 94 g and its $^1$H-NMR spectrum indicated only small traces of the complex.

Total yield: 44% based on the amount of ligand f2) Preparation of ethanediylbis(4,5,6,7-tetrahydroindenyl)zirconium bis(2,4,6-trimethylphenoxide) by hydrogenation without addition of amine 274.35 g (theoretically 41.8 mmol) of the solution obtained in reaction step e) were transferred under nitrogen into a 1000 ml autoclave provided with a hydrogen connection. 2.5 g of palladium on carbon were added to this solution. While stirring, the reactor was flushed three times with nitrogen and subsequently three times with hydrogen. The reactor was then heated to 80° C. and pressurized with 20 bar of hydrogen. After one hour, the pressure had dropped to about 17.5 bar as was once again increased to 20 bar. After 1.5 hours, the pressure had dropped to about 19 bar and was again brought back to 20 bar. After four hours, the pressure had dropped to about 18 bar and was again brought back to 20 bar. The $^1$H-NMR spectrum showed complete hydrogenation to ethanediylbis(4,5,6,7-tetrahydroindenyl)zirconium bis(2,4,6-trimethylphenoxide).

The reactor was subsequently cooled to room temperature under a hydrogen pressure of 10 bar over a period of half an hour. The suspension was transferred to a flask and filtered through a Seitz filter to separate off the hydrogenation catalyst. The filtrate was retained.

g2) Synthesis of ethanediylbis(4,5,6,7-tetrahydroindenyl)zirconium dichloride 6.6 g of acetyl chloride were slowly added at room temperature via a dropping funnel to the solution from reaction step f2). After the addition was complete, the suspension was stirred for 17 hours. The suspension was subsequently filtered and the filter cake was washed twice with 10 g of toluene and subsequently with 10 g of heptane and was then again washed with 10 g of toluene. The filter cake was dried under reduced pressure for a number of hours and had a mass of 6.9 g. The NMR spectrum showed pure racemic ethanediylbis(4,5,6,7-tetrahydroindenyl)zirconium dichloride. The filtrate had a mass of 331.5 g and was concentrated to 97.2 g at 40° C. and 100-150 mbar. Heptane was added to the concentrated filtrate. A white precipitate formed immediately and was filtered off and dried under reduced pressure for a number of hours. It had a mass of 0.5 g. The $^1$H-NMR spectrum showed the pure racemic complex.

Total yield: 42% based on the amount of ligand.

f3) Synthesis of ethanediylbis(4,5,6,7-tetrahydroindenyl)zirconium bis(2,4,6-trimethylphenoxide) by hydrogenation 548.7 g (theoretically 83.6 mmol) of the solution obtained in step e) was transferred under nitrogen to a 1000 ml autoclave provided with a hydrogen connection. 5 g of palladium on carbon were added to this solution. While stirring, the reactor was flushed three times with nitrogen and then three times with hydrogen. The reactor was subsequently heated to 80° C. and pressurized with 20 bar of hydrogen. After 1.5 hours, the pressure had dropped to 6 bar. The reaction was stopped, and the $^1$H-NMR spectrum showed complete hydrogenation to KL050. Stirring and heating were stopped and the reactor was cooled to room temperature. The suspension was transferred to a round-bottom flask and filtered through a Seitz filter to separate off the hydrogenation catalyst. The filtrate had a mass of 585.6 g. The filtrate was divided into three parts each having a mass of 146.4 g.

g3a) Synthesis of ethanediylbis(4,5,6,7-tetrahydroindenyl)zirconium dichloride with addition of acetyl chloride in 2 stages 1.95 g of acetyl chloride in 5 g of toluene were slowly added at room temperature via the dropping funnel to 146.4 g of the solution obtained in step f3). The reaction mixture was subsequently stirred at room temperature for one hour, after which a further 1.95 g of acetyl chloride in 5 g of toluene were added and the reaction mixture was stirred at room temperature for another 5.5 hours. During this time, a precipitate formed after about four hours. The reaction mixture was stirred for a further 12 hours. The suspension was subsequently concentrated to 30% of the original mass and then filtered through a filter No. 3. The precipitate was dried under reduced pressure for a number of hours and had a mass of 3.1 g. The $^1$H-NMR spectrum showed pure racemic complex. The filtrate had a mass of 46.9 g. Total yield: 35% based on ligand used.

g3b) Preparation of ethanediylbis(4,5,6,7-tetrahydroindenyl)zirconium dichloride with acetyl chloride addition in one step The preparation was carried out as in step g3a), except that the total amount of acetyl chloride (3.7 g) was added via the dropping funnel in one step at room temperature and the reaction mixture was stirred for five hours at 45° C. instead of room temperature. A precipitate formed after about two hours. The suspension was concentrated to 46% of the original mass and subsequently filtered through a filter No. 3. The precipitate was washed with small amounts of toluene and subsequently dried under reduced pressure for a number of hours. This gave a mass of 2.3 g. The $^1$H-NMR spectrum showed the formation of the pure racemic complex. The filtrate had a mass of 89.7 g. Total yield: 26% based on amount of ligand.

g3c) Synthesis of ethanediylbis(4,5,6,7-tetrahydroindenyl)zirconium dichloride with addition of undiluted acetyl chloride 3.7 g of acetyl chloride were added via the dropping funnel at 45° C. to 146.4 g of the reaction solution obtained from step f3). The reaction mixture was stirred at this temperature for two hours. A precipitate formed. The suspension was concentrated to approximately 60% of the original mass and was subsequently filtered through a filter No. 3. The precipitate was dried under reduced pressure for a number of hours and had a mass of 2.2 g. The $^1$H-NMR spectrum shows the formation of the pure racemic complex. The filtrate has a mass of 114.2 g. Total yield: 26% based on the amount of ligand used.

Example 4

Preparation of ethanediylbis(4,5,6,7-tetrahydroindenyl)zirconium bis(2,4,6-trimethylphenoxide) with isolation of the intermediate a) Preparation of ZrCl$_4$(THF)$_2$ The preparation was carried out as in step a) of the preceding examples. The amounts used were 46.6 g of ZrCl$_4$ (199.97 mmol), 80 g of toluene and 30.3 g of THF.

b) Preparation of Li(2,4,6-Me$_3$-C$_6$H$_2$O)

The preparation was carried out as in step b) of the preceding example. The amounts used were 56.3 g (413.42 mmol) of 2,4,6-trimethylphenol, 100 g of toluene, 29 g of THF and 124.3 g of BuLi solution.

c) Preparation of (THF)$_2$ Cl$_2$ Zr(2,4,6-Me$_3$-C$_6$H$_2$O)$_2$

The preparation was carried out as in step c) of the preceding example.

d) Preparation of ethane-1,2-diylbisindenyidilithium

The preparation was carried out as in step d) of the preceding example. The amounts used were 46.5 g (179.98 mmol) of 1,2-ethanediylbisindenyl, 80 g of toluene, 17.1 g of THF, 112.5 g of BuLi solution.

e) Preparation of ethanediylbis(indenyl)zirconium bis(2,4,6-trimethylphenoxide)

The preparation was carried out as in step e) of the preceding example, but the filter cake was washed with 40 g of toluene and a further 35 g of toluene. Theoretical concentration: 14.6%; mass of the filtrate: 750.7 g.

Isolation of ethanediylbis(indenyl)zirconium bis(2,4,6-trimethylphenoxide)

About 200 g of the solution obtained in step e) was concentrated to less than half its mass (123 g of the solvent were evaporated off). The complex crystallized from this solution after a number of hours at room temperature. The complex was isolated by filtration, washed with 5 ml of toluene and dried under reduced pressure. This gave 13.35 g of the complex. The mother liquor was concentrated further under reduced pressure, and gave a further 2.61 g of crystals after a number of days at room temperature. Total yield: 15.61 g (25.26 mmol); the yield in the overall reaction is therefore 52% (94.81 mmol).

f1) Preparation of ethanediylbis(4,5,6,7-tetrahydroindenyl)zirconium bis(2,4,6-trimethylphenoxide) by hydrogenation 557.6 g (theoretically 134 mmol) of the solution obtained in step e) were transferred under nitrogen to a 1000 ml autoclave provided with a hydrogen connection. 8 g of palladium on carbon were added to this solution. The stirrer was switched on and the reactor was flushed three times with nitrogen and then three times with hydrogen. The reactor was subsequently heated to 80° C. and pressurized with 20 bar of hydrogen. After 60 minutes, the pressure had dropped to about 0 bar and was once again brought back to 20 bar. After 1.5 hours, the pressure had dropped to 17 bar. The $^1$H-NMR spectrum showed complete hydrogenation to ethanediylbis (4,5,6,7-tetrahydroindenyl)zirconium bis(2,4,6-trimethylphenoxide) with only small traces of impurities. The reactor was cooled to 37° C. over a period of 1.5 hours. The suspension was transferred to a round-bottom flask and filtered through a Seitz filter to separate off the hydrogenation catalyst. The filter was washed with 20 g of toluene. The filtrate had a mass of 567.9 g.

Isolation of ethanediylbis(4,5,6,7-tetrahydroindenyl)zirconium bis(2,4,6-trimethylphenoxide)

155.36 g of the solution obtained in step f1) were concentrated to a considerable degree (to about 30 ml of solvent). The complex crystallized slowly at room temperature from the solution after a number of hours. The solution was concentrated further to about 20 ml and left a sticky oil. 50 ml of heptane were added at room temperature. The complex precipitated as white crystals. The flask was stored at −20° C. for three days and the precipitate was subsequently filtered off. Only 7.34 g of the complex could be isolated because of its very high solubility even in hydrocarbons.

Yield: 7.34 g (32.5%).

Example 5

Preparation of ethanediylbis(4,5,6,7-tetrahydroindenyl)zirconium 3,3',5,5'-tetra-tert-butyl-1,1'-bi-2-phenoxide via ethanediylbis(indenyl)zirconium 3,3',5,5'-tetra-tert-butyl-1,1'-bi-2-phenoxide a) Preparation of ZrCl$_4$(THF)$_2$ The preparation was carried out as in step a) of the preceding examples. The amounts used were 8.93 g of ZrCl$_4$ (38.32 mmol), 130 ml of toluene and 8.0 g of THF.

b) Preparation of Li$_2$(3,3',5,5'-tetra-tert-butyl-1,1'-bi-2-phenoxide)

In a dry 500 ml three-neck round-bottom flask which had been flushed with inert gas and was equipped with a magnetic stirrer bar, dropping funnel and vacuum connection with stopcock, 15.7 g (38.23 mmol) of 3,3',5,5'-tetra-tert-butyl-1,1'-bi-2-phenol were dissolved in 130 ml of toluene and 8 g of THF. The solution was cooled to about 4° C. in an ice bath and 28.4 ml of a 20% strength by weight BuLi solution were subsequently added dropwise via the dropping funnel over a period of one hour. After the addition was complete, the reaction mixture was allowed to warm to room temperature and was stirred for a further hour.

c) Preparation of (THF)$_2$Cl$_2$Zr(3,3',5,5'-tetra-tert-butyl-1,1'-bi-2-phenoxide)

The solution from step b) was introduced under nitrogen by means of a syringe into the suspension from step a) over a period of several minutes at room temperature. The suspension was stirred for a further four hours.

d) Preparation of ethane-1,2-diylbisindenyldilithium

In a dry 1000 ml three-neck round-bottom flask which had been flushed with inert gas and was equipped with a magnetic stirrer bar, dropping funnel and vacuum connection with stopcock, 9.5 g (36.77 mmol) of the indenyl were suspended in 120 ml of toluene and 7.0 g of THF. The suspension was cooled in an ice bath and 27.5 ml of a BuLi solution were then slowly added dropwise. The suspension was subsequently stirred at room temperature for a further 1.5 hours.

e) Preparation of ethanediylbis(indenyl)zirconium 3,3',5,5'-tetra-tert-butyl-1,1'-bi-2-phenoxide The suspension from step c) was introduced under nitrogen by means of a syringe into the suspension from step d). Residues which remained were washed out with 10 ml of toluene. The reaction mixture was stirred at room temperature for 12 hours, after which it was warmed to 80° C. At this temperature, the suspension was placed under nitrogen on a glass frit No. 4 and filtered into a round-bottom flask with stopcock. The filtrate was concentrated under reduced pressure with evaporation of 370 ml of solvent. The concentrated filtrate was allowed to stand at room temperature for a number of days without the complex crystallizing out. The solvent of the filtrate was removed completely under reduced pressure, giving a foam which was crushed to a powder.

30.5 g of the crude complex contaminated with LiCl were isolated.

Example 6

6.1 g (theoretically 9.2 mmol) of the crude ethanediylbis (indenyl)zirconium 3,3',5,5'-tetra-tert-butyl-1,1'-bi-2-phenoxide from the preceding example were dissolved in 232 g of toluene and transferred under nitrogen to a 1000 ml autoclave provided with a hydrogen connection. 0.11 g of palladium on carbon was added to this solution. The stirrer was switched on and the reactor was flushed three times with nitrogen and subsequently three times with hydrogen. The reactor was then heated to 40° C. and pressurized with 20 bar of hydrogen. After two hours, the pressure had dropped to about 18 bar and was once again increased to 20 bar. After three hours, the pressure had dropped to 18 bar and was again brought back to 20 bar. After a further six hours, the pressure had dropped to 18 bar and was again increased to 20 bar. A further 0.9 g of Pd/C in toluene was added. The reactor was once again pressurized with 20 bar of hydrogen for one hour, after which the pressure had dropped to 18 bar. After a further two hours, the reaction was stopped. The $^1$H-NMR spectrum showed complete formation of the hydrogenated complex ethanediylbis(4,5,6,7-tetrahydroindenyl)zirconium 3,3',5,5'-tetra-tert-butyl-1,1'-bi-2-phenoxide plus resonances which could be assigned to 3,3',5,5'-tetra-tert-butyl-1,1'-bi-2-phenol.

b) The reaction of the preceding step was repeated using 8.5 g (theoretically 11 mmol) of the crude starting complex which were dissolved in 300 g of $CH_2Cl_2$ and subsequently transferred under nitrogen to a 1000 ml autoclave with hydrogen connection. 0.15 g of palladium on carbon was added to this solution, the stirrer was started and the reactor was flushed three times with nitrogen and then three times with hydrogen. The reactor was heated to 5° C. and pressurized with 20 bar of hydrogen. After 90 minutes, the pressure had dropped to 17 bar and was once again increased to 20 bar. After 11 hours, the pressure was again increased to 20 bar and the temperature was increased to 60° C. After a further six hours, the pressure remained constant. Stirring and heating were stopped and the reactor was cooled to 25° C. and maintained at this temperature for 48 hours. The reactor was then heated again to 60° C. and pressurized with 20 bar of hydrogen. This pressure was maintained for 4.5 hours. The reactor was subsequently cooled to room temperature and the suspension was transferred to a round-bottom flask and filtered through a Seitz filter to separate off the hydrogenation catalyst. The solvent of the filtrate was evaporated, giving a beige foam. 10 ml of heptane were added to the foam. White crystals formed after a number of minutes. The flask was cooled to 2° C. and kept at this temperature for 4 hours. The precipitate was subsequently filtered off, washed with small amounts of heptane and subsequently dried under reduced pressure. 1.5 g of product were isolated. The $^1$H-NMR spectrum showed that the white precipitate consisted of pure rac-ethanediylbis(4,5,6,7-tetrahydroindenyl)zirconium 3,3',5,5'-tetra-tert-butyl-1,1'-bi-2-phenoxide. A further 0.1 g was obtained from the mother liquor. Yield: 18% (based on the amount of crude starting material).

Example 7

Synthesis of ethanediylbis(4,5,6,7-tetrahydroindenyl)zirconium dichloride via ethanediylbis(indenyl)zirconium bis(2,4-di-tert-butylphenoxide)

a) Preparation of $ZrCl_4(THF)_2$

In a dry 500 ml three-neck round-bottom flask which had been flushed with inert gas and was equipped with a magnetic stirrer bar, a dropping funnel and a vacuum connection with stopcock, 18 g (77.4 mmol) of zirconium tetrachloride were suspended in 40 g of toluene. At room temperature, 11.9 g of THF were slowly added via the dropping funnel over a period of 15 minutes. The suspension was stirred for a further one hour at room temperature.

b) Preparation of $Li(2,4-tBu_2-C_6H_3O)$

In a dry 500 ml three-neck round-bottom flask which had been flushed with inert gas and was equipped with a magnetic stirrer rod, a dropping funnel and a vacuum connection with stopcock, 32.9 g (154.8 mmol) of 2,4-di-tert-butylphenol were dissolved in 40 g of toluene and 9 g of THF. At room temperature, 50.6 g of a BuLi solution (20% by weight) were slowly added via the dropping funnel over a period of 15 minutes. The resulting suspension was stirred for a further one hour at room temperature.

c) Preparation of $(THF)_2Cl_2Zr(2,4-tBu_2C_6H_3O)_2$

The solution from step b) was added via a canula over a period of a number of minutes to the suspension from step a) at room temperature under nitrogen. Residual lithium phenoxide remaining in the round-bottom flask was rinsed out using 10 ml of toluene.

d) Preparation of ethane-1,2-diylbisindenyldilithium

In a dry 1000 ml three-neck round-bottom flask which had been flushed with inert gas and was equipped with magnetic stirrer bar, a dropping funnel and a vacuum connection with stopcock, 20 g (77.4 mmol) of 1,2-ethanediylbisindenyl were dissolved in 40 g of toluene and 7 g of THF. At room temperature, 50.8 g of a BuLi solution (20% by weight) were slowly added dropwise over a period of 20 minutes. The resulting suspension was stirred for a further 2.5 hours at room temperature.

e) Preparation of ethanediylbis(indenyl)zirconium bis(2,4-di-tert-butylphenoxide)

The suspension from step c) was added via a canula to the suspension from step d) under nitrogen. Residues remaining in the round-bottom flask were rinsed out using 10 ml of toluene. The resulting suspension was stirred overnight at room temperature and subsequently placed by means of a canula under nitrogen on a glass filter frit No. 4 which had been flushed with inert gas. The suspension was filtered into a 1000 ml round-bottom flask with stopcock and the filter cake was washed with 10 g of toluene.

f) Synthesis of ethanediylbis(4,5,6,7-tetrahydroindenyl)zirconium bis(2,4-di-tert-butylphenoxide) by hydrogenation The solution obtained in step e) was transferred under nitrogen into a 1000 ml autoclave provided with a hydrogen connection. 4.2 g of palladium on carbon were added to this solution. The stirrer was started and the reactor was flushed three times with nitrogen and subsequently three times with hydrogen. The reactor was heated to 80° C. and pressured with 20 bar of $H_2$. After one hour, the pressure had dropped to about 8 bar and was increased again to 20 bar. After two hours, the pressure had dropped to about 12 bar and was increased again to 20 bar. After 3 hours, the pressure had dropped to 10 bar and was again brought back to 20 bar. After 4 hours, the pressure had dropped to 11 bar and stirring and heating were stopped. The $^1$H-NMR spectrum showed complete hydrogenation of the starting compound to the target complex. The resulting solution was filtered. The filtrate had a mass of 306.4 g.)

g) Preparation of ethanediylbis(4,5,6,7-tetrahydroindenyl) zirconium dichloride 10.9 g of acetyl chloride were slowly added at room temperature via a dropping funnel to the solution obtained in step f). A precipitate formed during the addition of the acetyl chloride. The mixture as then allowed to stand for 56 hours at room temperature. The $^1$H-NMR spectrum showed no resonance which could be assigned to the starting complex (bisphenoxide). The suspension was subsequently filtered. The filter cake was dried under reduced pressure and had a mass of 17.5 g. The $^1$H-NMR spectrum indicated purely racemic ethanediylbis(4,5,6,7-tetrahydroindenyl)zirconium dichloride. The total yield is about 55% (based on the amount of starting material).

Comparative Example A

Synthesis of ethanediylbis(4,5,6,7-tetrahydroindenyl)zirconium dichloride via ethanediylbis(indenyl)zirconium (2,4-di-tert-butylphenoxide) chloride a) Preparation of ZrCl$_4$(THF)$_2$ In a dry 500 ml three-neck round-bottom flask which had been flushed with inert gas and was equipped with a magnetic stirrer bar, a dropping funnel and a vacuum connection with stopcock, 18 g (77.4 mmol) of zirconium tetrachloride were suspended in 40 g of toluene. At room temperature, 12 g of THF were slowly added via the dropping funnel over a period of 15 minutes. The suspension was stirred for a further one hour at room temperature.

b) Preparation of Li(2,4-tBu$_2$-C$_6$H$_3$O)

In a dry 500 ml three-neck round-bottom flask which had been flushed with inert gas and was equipped with a magnetic stirrer rod, a dropping funnel and a vacuum connection with stopcock, 16.5 g (77.6 mmol) of 2,4-ditertbutylphenol were dissolved in 20 g of toluene and 4.5 g of THF. At room temperature, 24.1 g of a BuLi solution (20% by weight) were slowly added via the dropping funnel over a period of 15 minutes. The resulting suspension was stirred for a further one hour at room temperature.

c) Preparation of (THF)$_2$Cl$_3$Zr(2,4-tBu$_2$C$_6$H$_3$O)

The solution from step b) was added via a canula over a period of a number of minutes to the suspension from step a) at room temperature under nitrogen. Residual lithium phenoxide remaining in the round-bottom flask was rinsed out using 10 ml of toluene.

d) Preparation of ethane-1,2-diylbisindenyldilithium

In a dry 1000 ml three-neck round-bottom flask which had been flushed with inert gas and was equipped with magnetic stirrer bar, dropping funnel and vacuum connection with stopcock, 20 g (77.4 mmol) of 1,2-ethanediyfbisindenyl were dissolved in 40 g of toluene and 7 g of THF. At room temperature, 50.8 g of a BuLi solution (20% by weight) were slowly added dropwise over a period of 20 minutes. The resulting suspension was stirred for a further 2.5 hours at room temperature.

e) Preparation of ethanediylbis(indenyl)zirconium (2,4-di-tert-butylphenoxide) chloride The suspension from step c) was added via a canula to the suspension from step d) under nitrogen. Residues remaining in the round-bottom flask were rinsed out using 10 ml of toluene. The resulting suspension was stirred overnight at room temperature and subsequently placed by means of a canula under nitrogen on a glass filter frit No. 4 which had been flushed with inert gas. The suspension was filtered into a 1000 ml round-bottom flask with stopcock and the filter cake was washed with 10 g of toluene.

f) Synthesis of ethanediylbis(4,5,6,7-tetrahydroindenyl)zirconium (2,4-ditertbutylphenoxide) chloride by hydrogenation The solution obtained in step e) was transferred under nitrogen into a 1000 ml autoclave provided with a hydrogen connection. 4.2 g of palladium on carbon were added to this solution. The stirrer was started and the reactor was flushed three times with nitrogen and subsequently three times with hydrogen. The reactor was heated to 80° C. and pressured with 20 bar of H$_2$. After one hour, the pressure had dropped to about 10 bar and was increased again to 20 bar. After two hours, the pressure had dropped to about 12 bar and was increased again to 20 bar. After 3 hours, the pressure had dropped to 16 bar, and subsequently stirring and heating were stopped. The $^1$H-NMR spectrum showed complete hydrogenation of the starting compound to the target complex. The resulting solution was filtered. The filtrate had a mass of 248 g.

g) Preparation of ethanediylbis(4,5,6,7-tetrahydroindenyl) zirconium dichloride 5.5 g of acetyl chloride were slowly added at room temperature via a dropping funnel to the solution obtained in step f). A precipitate formed during the addition of the acetyl chloride. The mixture was then allowed to stand for 18 hours at room temperature. 0.6 g of acetyl chloride was subsequently added via the dropping funnel and then the suspension was heated to 45° C. for 2 hours. The $^1$H-NMR spectrum showed no resonance which could be assigned to the starting complex (monophenoxide). The suspension was subsequently filtered. The filter cake was dried under reduced pressure and had a mass of 5 g. The $^1$H-NMR spectrum indicated purely racemic ethanediylbis(4,5,6,7-tetrahydro-indenyl)zirconium dichloride. The total yield is about 15% (based on the amount of starting material).

The invention claimed is:

1. A process for preparing partially hydrogenated, racemic ansa-metallocene complexes of formula VIa

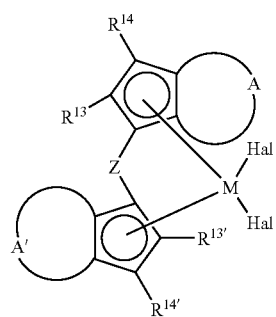

by reacting bridged or unbridged transition metal-aromatic complexes of the formula I

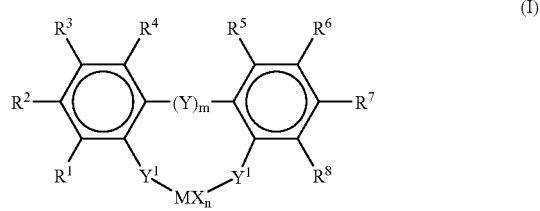

where the substituents and indices have the following meanings:

M is titanium, zirconium, hafnium, vanadium, niobium, tantalum, chromium, molybdenum, tungsten or an element of transition group III of the Periodic Table and the lanthanides, X are identical or different and are each fluorine, chlorine, bromine, iodine, hydrogen, $C_1$-$C_{10}$-alkyl, $C_6$-$C_{15}$-aryl, alkylaryl having from 1 to 10 carbon atoms in the alkyl part and from 6 to 20 carbon atoms in the aryl part, —$OR^{10}$ or —$NR^{10}R^{11}$, n is an integer from 1 to 4 and corresponds to the valence of M minus 2, $R^1$ to $R^8$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, where adjacent radicals from $R^2$ to $R^7$ may also form saturated, partially saturated or unsaturated cyclic groups having from 4 to 15 carbon atoms, $Si(R^9)_3$, —$OR^{10}$, —$SR^{10}$, —$N(R^{10})_2$, —$P(R^{10})_2$, and all the abovementioned radicals may be fully or partially substituted by heteroatoms, $R^9$ are identical or different and are each $C_1$-$C_{20}$-alkyl, $C_3$-$C_{10}$-cycloalkyl, $C_6$-$C_{15}$-aryl, where the radicals mentioned may be partially or fully substituted by heteroatoms, $R^{10}$ are identical or different and are each $C_1$-$C_{10}$-alkyl, $C_6$-$C_{15}$-aryl, $C_3$-$C_{10}$-cycloalkyl, alkylaryl or $Si(R^{11})_3$, $R^{11}$ are identical or different and are each $C_1$-$C_{10}$-alkyl, $C_6$-$C_{15}$-aryl, $C_3$-$C_{10}$-cycloalkyl, alkylaryl;

Y, $Y^1$ are identical or different and are each $$-\underset{\underset{R^{12}}{|}}{\overset{\overset{R^{12}}{|}}{M^1}}-,\quad -\underset{\underset{R^{12}}{|}}{\overset{\overset{R^{12}}{|}}{M^1}}-\underset{\underset{R^{12}}{|}}{\overset{\overset{R^{12}}{|}}{M^1}}-,\quad -\underset{\underset{R^{12}}{|}}{\overset{\overset{R^{12}}{|}}{M^1}}-CR_2^{12}-,$$

$$-\underset{\underset{R^{12}}{|}}{\overset{\overset{R^{12}}{|}}{C}}-,\quad -O-\underset{\underset{R^{12}}{|}}{\overset{\overset{R^{12}}{|}}{M^1}}-,\quad -\underset{\underset{R^{12}}{|}}{\overset{\overset{R^{12}}{|}}{C}}-\underset{\underset{R^{12}}{|}}{\overset{\overset{R^{12}}{|}}{C}}-,$$

or =$BR^{12}$, =$AlR^{12}$, —Ge—, —Sn—, —O—, —S—, =SO, =$SO_2$, =$NR^{12}$, =CO, =$PR^{12}$ or =$P(O)R^{12}$, where $R^{12}$ are identical or different and are each hydrogen, halogen, $C_1$-$C_{10}$-alkyl, $C_1$-$C_{10}$-fluoroalkyl, $C_6$-$C_{10}$-fluoroaryl, $C_6$-$C_{10}$-aryl, $C_1$-$C_{10}$-alkoxy, $C_2$-$C_{10}$-alkenyl, $C_7$-$C_{40}$-arylalkyl, $C_8$-$C_{40}$-arylalkenyl, $C_7$-$C_{40}$-alkylaryl, or two radicals $R^{12}$ together with the atoms connecting them form a ring, $M^1$ is silicon, germanium or tin and m is 0, 1, 2 or 3, or Y is nonbridging and represents two radicals R' and R" where R', R" are as defined for $R^1$ to $R^8$ and R', R" together with adjacent radicals $R^4$, $R^5$ may also form saturated, partially saturated or unsaturated cyclic groups having from 4 to 15 carbon atoms, with cyclopentadienyl derivatives of the formula II $$\left[\begin{array}{c}\text{structure with }R^{14}, R^{13}, T, Z, T', R^{13'}, R^{14'}\end{array}\right] pM^2 \quad\text{(II)}$$

where (divalent group diagram with T)

is a divalent group (structures with $R^{17}$, $R^{18}$, $R^{19}$, $R^{20}$) or (structure with $R^{17}$, $R^{18}$, $R^{19}$, S) or (structure with $R^{17}$, $R^{18}$, $R^{19}$, N)

and (divalent group diagram with T')

is a divalent group (structures with $R^{20'}$, $R^{19'}$, $R^{18'}$, $R^{17'}$) or (structure with $R^{18'}$, $R^{17'}$, S) or (structure with $R^{19'}$, $R^{18'}$, $R^{17'}$, N)

and the substituents and indices have the following meanings:

$R^{13}$, $R^{13'}$, $R^{14}$, $R^{14'}$ are identical or different and are each hydrogen, halogen, $C_1$-$C_{20}$-alkyl, 3- to 8-membered cycloalkyl which may in turn bear a $C_1$-$C_{10}$-alkyl group as substituent, $C_6$-$C_{15}$-aryl, alkylaryl having from 1 to 10 carbon atoms in the alkyl part and from 6 to 20 carbon atoms in the aryl part, arylalkyl having from 1 to 10 carbon atoms in the alkyl part and from 6 to 20 carbon atoms in the aryl part, —OR$^{10}$, —SR$^{10}$, —N(R$^{10}$)$_2$, —P(R$^{10}$)$_2$ or Si(R$^9$)$_3$, Z is a -[Q(R$^{15}$)(R$^{16}$)]$_q$- group, where Q may be identical or different and are each silicon, germanium, tin or carbon, R$^{15}$, R$^{16}$ are each hydrogen, C$_1$-C$_{10}$-alkyl, C$_3$-C$_{10}$-cycloalkyl or C$_6$-C$_{15}$-aryl, and q is 1, 2, 3 or 4;

R$^{17'}$-R$^{20}$, R$^{17'}$-R$^{20'}$ are identical or different and are each hydrogen, C$_1$-C$_{20}$-alkyl, 3- to 8-membered cycloalkyl which may in turn bear a C$_1$-C$_{10}$-alkyl group as substituent, C$_6$-C$_{15}$-aryl or arylalkyl, where adjacent radicals may together form cyclic groups having from 4 to 15 carbon atoms, or Si(R$^{11}$)$_3$, and M$^2$ is an alkali metal ion or alkaline earth metal ion, and p is 1 when M$^2$ is an alkaline earth metal ion and is 2 when M$^2$ is an alkali metal ion;

and heating the resulting reaction mixture to a temperature in the range from minus 78° C. to 250° C., with or without addition of free radicals or free radical formers, to give a complex of the formula III

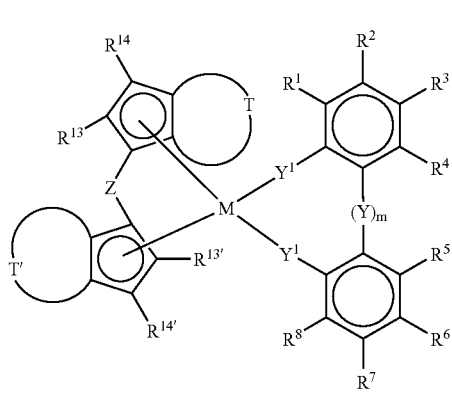

(III)

and at least partially hydrogenating III by means of hydrogen in the presence of a suitable catalyst to a complex of formula VI

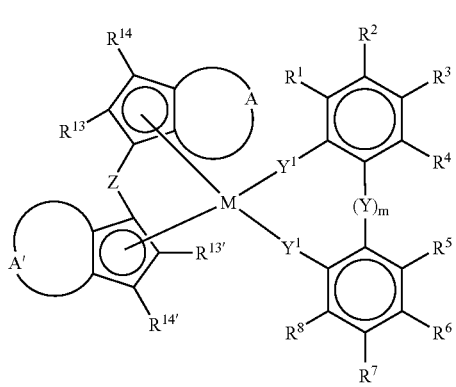

(VI)

and replacing the bridged phenoxide-analogous ligand or the two phenoxide-analogous ligands to give the complexes of formula VIa where

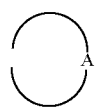

is a divalent group

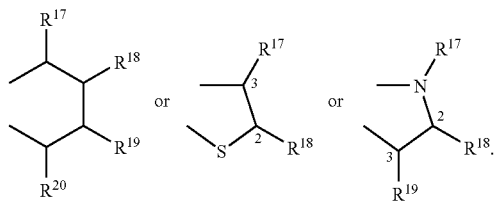

and

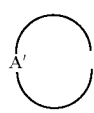

is a divalent group

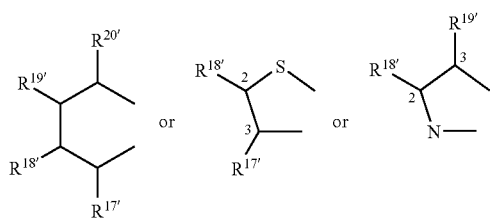

and

Hal is fluorine, chlorine, bromine or iodine.

2. A process as claimed in claim 1, wherein Y$^1$ are identical and are each oxygen.

3. A process as claimed in claim 1, wherein the hydrogenation is carried out in the presence of homogeneous or heterogeneous catalysts and optionally on suitable catalyst supports.

4. A process as claimed in claim 1, wherein the complex of the formula I is firstly prepared by deprotonation of compounds of the formula IV

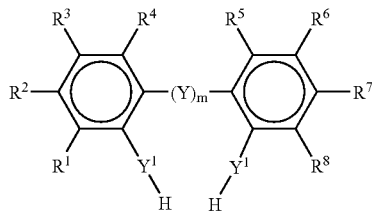

(IV)

and subsequent reaction of the deprotonated compound(s) with a suitable transition metal compound of formula V $$MX_4(\text{Lewis base})_k \qquad (V)$$

where all radicals are as defined in claim 1 and k is o, 1 or 2, and the complex of the formula 1 prepared in this way is converted in the reaction solution without isolation of intermediates into the complex of the formula IV.

5. A process as claimed in claim 1, for preparing ethanediylbis(4,5,6,7-tetrahydroindenyl)zirconium dichloride (compound of formula VIa), wherein a dihalozirconium bis(2,4,6-trimethylphenoxide) compound (compound of formula I) is reacted with ethane-1,2-diylbisindenyldilithium (compound of formula II) to form ethanediylbis(indenyl)zirconium bis(2,4,6-trimethylphenoxide) (compound of formula III) which is subsequently hydrogenated to ethanediyl-bis(4,5,6,7-tetrahydroindenyl)zirconium bis(2,4,6-trimethylphenoxide) (compound of formula VI) and the phenoxide groups are subsequently replaced.

6. A process as claimed in claim 1, for preparing ethanediylbis(4,5,6,7-tetrahydroindenyl)zirconium dichloride (compound of formula VIa), wherein a dihalozirconium bis(2,4-di-tert-butylphenoxide) compound (compound of formula I) is reacted with ethane-1,2-diybisindenyldilithium (compound of formula II) to form ethanediylbis(indenyl)zirconium bis(2,4-di-tert-butylphenoxide) (compound of formula III) which is subsequently hydrogenated to ethanediyl-bis(4,5,6,7-tetrahydroindenyl)zirconium bis(2,4-di-tert butylphenoxide) (compound of formula VI) and the phenoxide groups are subsequently replaced.

7. A process as claimed in claim 2, wherein the hydrogenation is carried out in the presence of homogeneous or heterogeneous catalysts which contain Pt, Pd, Rh, Ru, Os or nickel, Raney nickel, their oxides, salts or complexes, mixtures thereof, and optionally on a catalyst support, and in the presence of Pd on activated carbon.

* * * * *